United States Patent
Schnabel et al.

(10) Patent No.: US 6,498,253 B1
(45) Date of Patent: Dec. 24, 2002

(54) ACYLATED AMINOPHENYLSULFONYLUREAS, PROCESSES FOR THEIR PREPARATION AND THEIR USE AS HERBICIDES AND PLANT GROWTH REGULATORS

(75) Inventors: Gerhard Schnabel, Grosswallstadt (DE); Lothar Willms, Hofheim (DE); Klaus Bauer, Hanau (DE); Hermann Bieringer, Eppstein (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/257,669

(22) Filed: Feb. 25, 1999

Related U.S. Application Data

(62) Division of application No. 08/906,238, filed on Aug. 4, 1997, now Pat. No. 5,922,646, which is a continuation of application No. 08/429,933, filed on Apr. 27, 1995, now abandoned.

(30) Foreign Application Priority Data

Apr. 29, 1994 (DE) .......................... 44 15 049

(51) Int. Cl.[7] ..................... C07D 239/69; C07C 311/38; A01N 43/54
(52) U.S. Cl. ..................... 544/321; 544/331; 544/332; 544/122; 544/123; 544/238; 544/295; 544/296; 560/13; 564/26; 564/49; 564/74; 564/79; 564/83; 564/85; 564/86; 504/214; 504/215
(58) Field of Search ................. 544/321, 331, 544/332, 122, 123, 295, 296, 238; 540/601; 560/13; 564/26, 49, 74, 29, 83, 85, 86

(56) References Cited

U.S. PATENT DOCUMENTS

| | | | | |
|---|---|---|---|---|
| 2,910,488 A | * | 10/1959 | Novello et al. ........... 260/397.7 |
| 4,383,113 A | | 5/1983 | Levitt ......................... 544/211 |
| 4,394,506 A | | 7/1983 | Levitt ......................... 544/321 |
| 4,664,695 A | | 5/1987 | Schorter et al. ............ 544/343 |
| 4,892,946 A | | 1/1990 | Levitt ......................... 544/321 |
| 4,981,509 A | | 1/1991 | Hillemann .................. 544/211 |

FOREIGN PATENT DOCUMENTS

| | | |
|---|---|---|
| DE | 39 30 663 | 11/1990 |
| DE | 43 07 423 | 10/1993 |
| EP | PA 0 001 515 A3 | 5/1979 |
| EP | PA 0 007 687 A1 | 2/1980 |
| EP | PA 0 030 138 A1 | 6/1981 |
| EP | PA 0 116 518 A1 | 8/1984 |
| WO | WO 94/10105 | 5/1994 |
| WO | WO 94/10154 | 5/1994 |
| WO | WO 94/00423 | 6/1994 |

OTHER PUBLICATIONS

English Abstract No. 4220082—A published June 19, 1992 which relates to WO 94/00423.

\* cited by examiner

*Primary Examiner*—Richard L. Raymond
*Assistant Examiner*—Venkataraman Balasubramanian
(74) *Attorney, Agent, or Firm*—Frommer Lawrence & Haug LLP

(57) ABSTRACT

Compounds of the formula (I) and salts thereof (I)

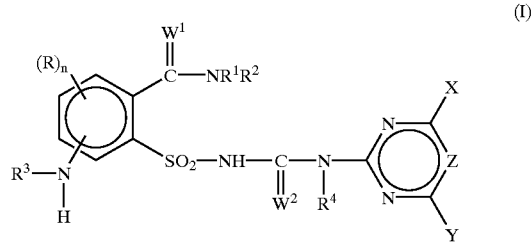

in which $W^1$, $W^2$, R, n, $R^1$, $R^2$, $R^4$, X, Y and Z are as defined in claim 1 and $R^3$ is an acyl radical, are suitable as herbicides and plant growth regulators. The herbicides can be prepared by the process variants from claim 5, the novel intermediate products (II), (IV), (VI) and (VIII)* of claims 9 and 10 being employed.

30 Claims, No Drawings

ACYLATED AMINOPHENYLSULFONYLUREAS, PROCESSES FOR THEIR PREPARATION AND THEIR USE AS HERBICIDES AND PLANT GROWTH REGULATORS

This application is a divisional of application U.S. Ser. No. 08/906,238, filed on Aug. 4, 1997, now U.S. Pat. No. 5,922,646, which is a continuing application of U.S. Ser. No. 08/429,933, filed on Apr. 27, 1995, now abandoned.

Acylated aminophenylsulfonylureas, processes for their preparation and their use as herbicides and plant growth regulators.

The invention relates to the technical field of herbicides and plant growth regulators, in particular herbicides for selective combating of broad-leaved weeds and graminaceous weeds in crops of useful plants.

It is known that phenylsulfonylureas which are substituted by heterocyclic substituents and carry an amino or a functionalized amino group on the phenyl ring have herbicidal and plant growth regulating properties (EP-A-1515; EP-A-7687 (=U.S. Pat. No. 4,383,113); EP-A-30138 (=U.S. Pat. No. 4,394,506); U.S. Pat. No. 4,892,946; U.S. Pat. No. 4,981,509; EP-A-116518 (=U.S. Pat. No. 4,664,695, U.S. Pat. No. 4,632,695)).

Phenylsulfonylureas which contain, on the phenyl ring, a carboxyl group or a function derived from the carboxyl group in the 2-position and an N-alkyl-N-acyl-amino group in the 5-position have furthermore already been proposed in German Patent Application P 42 36 902.9 (WO-94/10154).

Surprisingly, it has now been found that certain phenylsulfonyl ureas which are substituted by heterocyclic substituents are particularly suitable as herbicides and plant growth regulators.

The present invention relates to compounds of the formula (I) and salts thereof

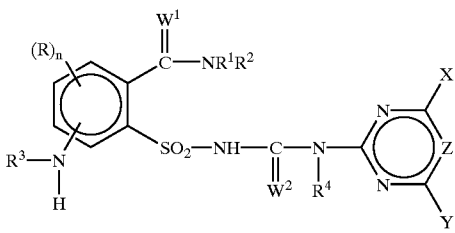

(I)

in which
W$^1$ is an oxygen or sulfur atom,
W$^2$ is an oxygen or sulfur atom,
n is 0, 1, 2 or 3, preferably 0 or 1, in particular 0,
R is halogen, alkyl or alkoxy, independently of other substituents R if n is greater than 1,
R$^1$ is hydrogen or an unsubstituted or substituted hydrocarbon or hydrocarbonoxy radical,
R$^2$ is hydrogen or an unsubstituted or substituted hydrocarbon radical,
or the group
NR$^1$R$^2$ is a heterocyclic ring having 3 to 8 ring atoms, which is unsubstituted or substituted and contains the N atom of the group NR$^1$R$^2$ as a hetero-ring atom and can also contain further hetero-ring atoms,
R$^3$ is an acyl radical,
R$^4$ is hydrogen or an aliphatic hydrocarbon radical,
X, Y independently of one another are halogen, C$_1$–C$_6$-alkyl, C$_1$–C$_6$-alkoxy, C$_1$–C$_6$-alkylthio, where each of the last three radicals mentioned is unsubstituted or substituted by one or more radicals from the group consisting of halogen, C$_1$–C$_4$-alkoxy and C$_1$–C$_4$-alkylthio, or are C$_3$–C$_6$-cycloalkyl, C$_2$–C$_6$-alkenyl, C$_2$–C$_6$-alkynyl, C$_3$–C$_6$-alkenyloxy or C$_3$–C$_6$-alkynyloxy, and
Z is CH or N.

In formula (I) and in the formulae used below, the alkyl, alkoxy, haloalkyl, haloalkoxy, alkylamino and alkylthio radicals and the corresponding unsaturated and/or substituted radicals can be in each case straight-chain or branched in the carbon skeleton. If not stated specifically, the lower carbon skeletons, for example having 1 to 4 carbon atoms or, in the case of unsaturated groups, having 2 to 4 carbon atoms, are preferred for these radicals. Alkyl radicals, including those in the composite meanings, such as alkoxy, haloalkyl and the like, are, for example, methyl, ethyl, n- or i-propyl, n-, i-, t- or 2-butyl, pentyl radicals, hexyl radicals, such as n-hexyl, i-hexyl and 1,3-dimethylbutyl, and heptyl radicals, such as n-heptyl, 1-methylhexyl and 1,4-dimethylpentyl; alkenyl and alkynyl radicals have the meaning of the possible unsaturated radicals corresponding to the alkyl radicals, and alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; and alkynyl is, for example, propargyl, but-2-yn-1-yl, but-3-yn-1-yl or 1-methylbut-3-yn-1-yl.

Halogen is, for example, fluorine, chlorine, bromine or iodine. Haloalkyl, -alkenyl and -alkynyl are alkyl, alkenyl or alkynyl which are partly or completely substituted by halogen, preferably by fluorine, chlorine and/or bromine, in particular by fluorine or chlorine, for example CF$_3$, CHF$_2$, CH$_2$F, CF$_3$CF$_2$, CH$_2$FCHCl, CCl$_3$, CHCl$_2$ and CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; corresponding statements apply to haloalkenyl and other radicals substituted by halogen.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl, preferably alkyl, alkenyl or alkynyl having up to 12 carbon atoms or cycloalkyl having 5 or 6 ring atoms or phenyl; corresponding statements apply to a hydrocarbonoxy radical.

Aryl is a mono-, bi- or polycyclic aromatic system, for example phenyl, naphthyl, tetrahydronaphthyl, indenyl, indanyl, pentalenyl, fluorenyl and the like, preferably phenyl; aryloxy is preferably an oxy radical corresponding to the aryl radical mentioned, in particular phenoxy.

Heteroaryl or a heteroaromatic radical is a mono-, bi- or polycyclic aromatic system in which at least 1 ring contains one or more heteroatoms, for example pyridyl, pyrimidinyl, pyridazinyl, pyrazinyl, thienyl, thiazolyl, oxazolyl, furyl, pyrrolyl, pyrazolyl and imidazolyl, and also bicyclic or polycyclic aromatic or araliphatic compounds, for example quinolinyl, benzoxazolyl and the like. Heteroaryl also includes a heteroaromatic ring, which is preferably 5- or 6-membered and contains 1, 2 or 3 hetero-ring atoms, in particular from the group consisting of N, O and S. In the substituted case, the heteroaromatic ring can also be benzofused.

A heterocyclic radical or ring can be saturated, unsaturated or heteroaromatic; it contains one or more hetero-ring atoms, preferably from the group consisting of N, O and S; it is preferably 5- or 6-membered and contains 1, 2 or 3 hetero-ring atoms. The radical can be, for example, a heteroaromatic radical or ring as defined above, or is a partly hydrogenated radical, such as oxiranyl, pyrrolidyl, piperidyl, piperazinyl, dioxolanyl, morpholinyl or tetrahydrofuryl.

Possible substituents for a substituted heterocyclic radical are the substituents mentioned below, and in addition also oxo. The oxo group can also occur on the hetero-ring atoms which can exist at various oxidation levels, for example in the case of N and S.

Substituted radicals, such as substituted hydrocarbon radicals, for example substituted alkyl, alkenyl, alkynyl, aryl, phenyl and benzyl, or substituted heteroaryl, a substituted bicyclic radical or ring or a substituted bicyclic radical, if appropriate with aromatic moieties, are, for example, a substituted radical which is derived from the unsubstituted parent substance, in which the substituents are, for example, one or more, preferably 1, 2 or 3, radicals from the group consisting of halogen, alkoxy, haloalkoxy, alkylthio, hydroxy, amino, nitro, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and the unsaturated aliphatic radicals corresponding to the saturated hydrocarbon-containing radicals mentioned, such as alkenyl, alkynyl, alkenyloxy, alkynyloxy and the like. In the case of radicals with carbon atoms, those having 1 to 4 carbon atoms, in particular 1 or 2 carbon atoms, are preferred. Substituents from the group consisting of halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano are as a rule preferred. The substituents methyl, methoxy and chlorine are particularly preferred here.

Mono- or disubstituted amino is, for example, alkylamino, dialkylamino, acylamino, arylamino or N-aryl-N-alkylamino.

Optionally substituted phenyl is preferably phenyl which is unsubstituted or substituted once or several times, preferably up to three times by identical or different radicals from the group consisting of halogen, $C_1$–$C_4$-alkyl, $C_1$–$C_4$-alkoxy, $C_1$–$C_4$-haloalkyl, $C_1$–$C_4$-haloalkoxy and nitro, for example o-, m- and p-tolyl, dimethylphenyl 2-, 3- and 4-chlorophenyl, 2-, 3- and 4-trifluoro- and -trichlorophenyl, 2,4-, 3,5-, 2,5- and 2,3-dichlorophenyl and o-, m- and p-methoxyphenyl.

An acyl radical is the radical of an organic acid, for example the radical of a carboxylic acid, and radicals of acids derived therefrom, such as thiocarboxylic acid or optionally N-substituted iminocarboxylic acids, or the radical of carbonic acid monoesters, optionally N-substituted carbamic acid, sulfonic acids, sulfinic acids, phosphonic acids, or phosphinic acids. Acyl is, for example, formyl, alkylcarbonyl, such as ($C_1$–$C_4$-alkyl)-carbonyl, phenylcarbonyl, in which the phenyl ring can be substituted, for example as indicated above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also relates to all the stereoisomers included by formula (I) and mixtures thereof. Such compounds of the formula (I) contain one or more asymmetric C atoms or also double bonds, which are not shown separately in the formula (I). The possible stereoisomers defined by their specific spatial form, such as enantiomers, diastereomers and Z and E isomers, are all included by the formula (I) and can be obtained from mixtures of the stereoisomers by customary methods, or can otherwise be prepared by stereoselective reactions in combination with the use of stereochemically pure starting substances.

The compounds of the formula (I) can form salts in which the hydrogen of the —$SO_2$—NH group or also other acidic hydrogen atoms (for example from COOH and the like) is replaced by a cation suitable for agriculture. These salts are, for example, metal salts, preferably alkali metal or alkaline earth metal salts, in particular sodium salts and potassium salts, or also ammonium salts or salts with organic amines. Salt formation can also be carried out by addition of an acid onto basic groups, such as, for example, amino and alkylamino. Suitable acids for this purpose are strong inorganic and organic acids, for example HCl, HBr, $H_2SO_4$ or $HNO_3$. Compounds of the formula (I) according to the invention or salts thereof which are of particular interest are those in which $R^1$ is H or alkyl, alkenyl, alkynyl, alkoxy, alkenoxy, alkynoxy, cycloalkyl, cycloalkenyl or phenyl, where each of the nine radicals mentioned last is unsubstituted or substituted and contains a total of up to 24 carbon atoms, preferably up to a total of 12, in particular up to a total of 8 carbon atoms, $R^2$ is H or alkyl, alkenyl or alkynyl, where each of the three radicals mentioned last is unsubstituted or substituted and contains a total of up to 24 carbon atoms, preferably up to a total of 12 carbon atoms, in particular up to a total of 8 carbon atoms, or the group $NR^1R^2$ is an unsubstituted or substituted heterocyclic ring of four to eight ring atoms, where the group contains up to a total of 18 carbon atoms, preferably up to a total of 12 carbon atoms, $R^3$ is acyl having up to 24 carbon atoms, preferably up to 12 carbon atoms, in particular up to 8 carbon atoms, and $R^4$ is H or alkyl, alkenyl or alkynyl, where each of the 3 radicals mentioned last contains up to 12 carbon atoms, preferably up to 5 carbon atoms.

Compounds of the formula (I) according to the invention or salts thereof which are of particular interest are those in which $R^1$ is H, $C_1$–$C_{12}$-alkyl, $C_2$–$C_{12}$-alkenyl, $C_2$–$C_{12}$-alkynyl, $C_1$–$C_{12}$-alkoxy, $C_2$–$C_{12}$-alkenoxy, $C_2$–$C_{12}$-alkynoxy, $C_3$–$C_8$-cycloalkyl or $C_5$–$C_8$-cycloalkenyl, where each of the eight radicals mentioned last is unsubstituted or substituted, for example is substituted by one or more radicals from the group consisting of halogen, cyano, azido, CO—$R^5$, $OR^6$, $NR^7R^8$, $SR^9$, SO—$R^{10}$ and $SO_2$—$R^{11}$, or unsubstituted or substituted phenyl, is H, $C_1$–$C_{12}$-alkyl, $C_2$–$C_{12}$-alkenyl or $C_2$–$C_{12}$-alkynyl, where each of the three radicals mentioned last is unsubstituted or substituted, for example is substituted by one or more radicals from the group consisting of halogen, cyano, azido, $COR^{12}$, $OR^{13}$, $NR^{14}R^{15}$, $SR^{16}$, SO—$R^{17}$ and $SO_2$—$R^{18}$, or the group $NR^1R^2$ is a heterocyclic ring of four to eight ring atoms, which can contain up to two further hetero-ring atoms in the ring from the group consisting of N, O and S and is unsubstituted or substituted by one or more radicals from the group consisting of halogen, $C_1$–$C_6$-alkyl, $NO_2$, $N_3$ and CN, $R^3$ is CO—$R^{19}$, CS—$R^{20}$, $SO_2$—$R^{21}$, SO—$R^{21}$ or $C(=NR^{21})$—$R^{19}$, $R^4$ is H, $C_1$–$C_3$-alkyl, $C_2$–$C_5$-alkenyl or $C_2$–$C_5$-alkynyl, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, $NR^{22}R^{23}$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or COO$CH_3$, $R^8$ is H, $C_1$–$C_5$-alkyl, $C_2$–$C_5$-alkenyl or $C_2$–$C_5$-alkynyl or the group $NR^7R^8$ is a heterocyclic ring of four to eight ring atoms, which can contain up to two further hetero-ring atoms in the ring from the group consisting of N, O and S and is unsubstituted or substituted by one or more radicals from the group consisting of halogen, $C_1$–$C_6$-alkyl, $NO_2$, $N_3$ and CN, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical analogous to $R^5$, $R^{13}$ is a radical analogous to $R^6$, $R^{14}$ is a radical analogous to $R^7$, $R^{15}$ is a radical analogous to $R^8$, or the group $NR^{14}R^{15}$ is a group analogous to $NR^7R^8$, $R^{16}$ is a radical analogous to $R^9$, $R^{17}$ is a radical analogous to $R^{10}$, $R^{18}$ is a radical analogous to $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di ($C_1$–$C_6$-alkyl)amino, N—$C_1$–$C_4$-alkoxy-N—$C_1$–$C_4$-alkylamino, where each of the 13 radicals mentioned last are unsubstituted or substituted, for example is substituted by one or more radicals from the group consisting of halogen, cyano, azido, CO—$R^{24}$, $OR^{25}$, $NR^{26}R^{27}$, $SR^{28}$, $SOR^{29}$ and $SO_2R^{30}$, or an unsubstituted or substituted phenyl, phenoxy or phenylamino radical, $R^{20}$ is a radical analogous to $R^{19}$, $R^{21}$ is a radical analogous to $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the 6 radicals mentioned last is unsubstituted or substituted, for example is substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the 5 radicals mentioned last is unsubstituted or substituted, for example is substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $NR^{22}R^{23}$ is a heterocyclic ring analogous to $NR^7R^8$, preferably a ring of 5 or 6 ring atoms, which can contain up to 2 further hetero-ring atoms in the ring from the group consisting of N, O and S and is unsubstituted or substituted by one or more radicals from the group consisting of halogen and $C_1$–$C_4$-alkyl, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H, $C_1$–$C_3$-alkyl, or the group $NR^{26}R^{27}$ is a group analogous to $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, $R^{30}$ is analogous to $R^{29}$, $W^1$ is O or S, preferably O, $W^2$ is O or S, preferably O, X, Y independently of one another are halogen, $C_1$–$C_4$-alkyl, $C_1$–$C_4$-alkoxy or $C_1$–$C_4$-alkylthio, where each of the three radicals mentioned last is unsubstituted or substituted by one or more radicals from the group consisting of halogen, $C_1$–$C_4$-alkoxy and $C_1$–$C_4$-alkylthio, or are mono- or di($C_1$–$C_4$-alkyl)amino, $C_3$–$C_6$-cycloalkyl, $C_3$–$C_5$-alkenyl or $C_3$–$C_5$-alkynyloxy, and Z is CH or N.

Preferred compounds of the formula (I) according to the invention or salts thereof are those in which $R^1$ is H, $C_1$–$C_6$-alkyl, $C_2$–$C_6$-alkenyl, $C_2$–$C_6$-alkynyl, $C_1$–$C_6$-alkoxy, $C_2$–$C_6$-alkenoxy, $C_2$–$C_6$-alkynoxy or $C_5$–$C_6$-cycloalkyl, where each of the 7 radicals mentioned last is unsubstituted or substituted, by one or more radicals from the group consisting of halogen, cyano, azido, CO—$R^5$, $OR^6$, $NR^7R^8$, $SR^9$, SO—$R^{10}$ and $SO_2$—$R^{11}$, or phenyl, which is unsubstituted or substituted by radicals from the group consisting of halogen, $C_1$–$C_4$-alkyl, $C_1$–$C_4$-alkoxy, $C_1$–$C_4$-haloalkyl, $C_1$–$C_4$-haloalkoxy and nitro, $R^2$ is H, $C_1$–$C_6$-alkyl, $C_2$–$C_6$-alkenyl or $C_2$–$C_6$-alkynyl, where each of the three radicals mentioned last is unsubstituted or substituted by one or more radicals from the group consisting of halogen, cyano, azido, $COR^{12}$, $OR^{13}$, $NR^{14}R^{15}$, $SR^{16}$, SO—$R^{17}$ and $SO_2$—$R^{18}$, or the group $NR^1R^2$ is a heterocyclic ring of 5 or 6 ring atoms, which can contain up to two further hetero-ring atoms in the ring from the group consisting of N and O and is unsubstituted or substituted by one or more radicals from the group consisting of $C_1$–$C_4$-alkyl, $R^3$ is CO—$R^{19}$, CS—$R^{20}$, $SO_2$—$R^{21}$ or C (=$NR^{21}$)—$R^{19}$, $R^4$ is H or $CH_3$, $R^5$ is H, $C_1$–$C_3$-alkyl, $C_1$–$C_3$-alkoxy, $NR^{22}R^{23}$ or OH, $R^6$ is H, $C_1$–$C_4$-alkyl or $C_1$–$C_4$-haloalkyl, $R^7$ is H, $C_1$–$C_3$-alkyl, $C_1$–$C_3$-alkoxy, CO—$CH_3$, CO—H or COO$CH_3$, $R^8$ is H or $C_1$–$C_3$-alkyl, or the group $NR^7R^8$ is a heterocyclic ring of 5 or 6 ring atoms, which can contain up to two further hetero-ring atoms in the ring from the group consisting of N and O and is unsubstituted or substituted by one or more $C_1$–$C_4$-alkyl radicals, $R^9$ is H, $C_1$–$C_3$-alkyl or $C_1$–$C_3$-haloalkyl, $R^{10}$ is $C_1$–$C_3$-alkyl or $C_1$–$C_3$-haloalkyl, $R^{11}$ $C_1$–$C_3$-alkyl, $C_1$–$C_3$-haloalkyl, $C_1$–$C_3$-alkoxy-$C_1$–$C_2$-alkyl, $R^{12}$ is a radical analogous to $R^5$, $R^{13}$ is a radical analogous to $R^6$, $R^{14}$ is a radical analogous to $R^7$, $R^{15}$ is a radical analogous to $R^8$, or the group $NR^{14}R^{15}$ is a group analogous to $NR^7R^8$, $R^{16}$ is a radical analogous to $R^9$, $R^{17}$ is a radical analogous to $R^{10}$, $R^{18}$ is a radical analogous to $R^{11}$, $R^{19}$ is H, $C_1-C_6$-alkyl, $C_2-C_6$-alkenyl, $C_2-C_6$-alkynyl, $C_1-C_6$-alkoxy, $C_1-C_6$-alkylthio, $C_2-C_6$-alkenoxy, $C_2-C_6$-alkynoxy, $C_3-C_6$-cycloalkyl, $C_1-C_6$-alkylamino, di-$(C_1-C_4$-alkyl)amino or N—$C_1-C_4$-alkoxy-N—$C_1-C_4$-alkylamino, where each of the 11 radicals mentioned last is unsubstituted or substituted by one or more radicals from the group consisting of halogen, cyano, CO—$R^{24}$, $OR^{25}$, $NR^{26}R^{27}$, $SR^{28}$, $SOR^{29}$ and $SO_2R^{30}$, or a phenyl, phenoxy or phenylamino radical, which is unsubstituted or substituted by radicals from the group consisting of halogen, $C_1-C_4$-alkyl, $C_1-C_4$-alkoxy, $C_1-C_4$-haloalkyl, $C_1-C_4$-haloalkoxy and nitro, $R^{20}$ is a radical analogous to $R^{19}$, $R^{21}$ is a radical analogous to $R^{11}$, $R^{22}$ is H $C_1-C_4$-alkyl or $C_1-C_4$-alkoxy, where each of the 2 radicals mentioned last is unsubstituted or substituted by one or more radicals from the group consisting of halogen, cyano, amino, mono- and di-$(C_1-C_4$-alkyl)amino, $C_1-C_3$-alkoxy, $C_1-C_3$-alkylsulfonyl, and $C_1-C_3$-alkylthio, $R^{23}$ is H, $C_1-C_5$-alkyl, $C_2-C_5$-alkenyl, $C_2-C_5$-alkynyl, $C_1-C_5$-alkoxy or $C_2-C_5$-alkenoxy, where each of the 5 radicals mentioned last is unsubstituted or substituted, for example is substituted by one or more radicals from the group consisting of halogen, cyano, azido, amino, mono- and disubstituted amino, $C_1-C_3$-alkyl, $C_1-C_3$-alkoxy, $C_1-C_3$-alkylthio, $C_1-C_3$-alkylsulfonyl and $C_1-C_3$-alkylsulfinyl, or the group $NR^{22}R^{23}$ is a group analogous to $NR^7R^8$, $R^{24}$ is H, $C_1-C_3$-alkyl, $C_1-C_3$-alkoxy, $NH_2$ or mono- or di-$(C_1-C_4$-alkyl)amino, $R^{25}$ is H, $C_1-C_5$-alkyl or $C_1-C_5$-haloalkyl, $R^{26}$ is H or $C_1-C_3$-alkyl, $R^{27}$ is H or $C_1-C_3$-alkyl, or the group $NR^{26}R^{27}$ is a group analogous to $NR^{22}R^{23}$, $R^{28}$ is H or $C_1-C_3$-alkyl, $R^{29}$ is $C_1-C_5$-alkyl or $C_1-C_5$-haloalkyl, $R^{30}$ is analogous to $R^{29}$, $W^1$ is O or S, preferably O, $W^2$ is O or S, preferably O, one of the radicals X and Y is halogen, $C_1-C_2$-alkyl, $C_1-C_2$-alkoxy, $C_1-C_4$-alkylthio, where each of the three radicals mentioned last is unsubstituted or substituted by one or more radicals from the group consisting of halogen, $C_1-C_2$-alkoxy and $C_1-C_2$-alkylthio, or mono- or di($C_1-C_2$-alkyl)amino, preferably halogen, methyl or methoxy, and the other of the radicals X and Y is $C_1-C_2$-alkyl, $C_1-C_2$-haloalkyl, $C_1-C_2$-alkoxy, $C_1-C_2$-haloalkoxy or $C_1-C_2$-alkylthio, preferably methyl or methoxy, and Z is CH or N, preferably CH.

Particularly preferred compounds of the formula (I) according to the invention or salts thereof are those in which $R^1$ is H, $C_1-C_2$-alkyl, $C_1-C_2$-alkoxy or phenyl, which is unsubstituted or substituted by one or more radicals from the group consisting of halogen, $C_1-C_2$-alkyl, $C_1-C_2$-alkoxy, $C_1-C_2$-haloalkyl and $C_1-C_2$-haloalkoxy, $R^2$ is H, $C_1-C_2$-alkyl or $C_1-C_2$-alkoxy, or the group $NR^1R^2$ is a heterocyclic ring of 5 or 6 ring atoms, which can contain up to one further hetero-ring atom in the ring from the group consisting of N and O and is unsubstituted or substituted by one or more $C_1-C_2$-alkyl radicals, $R^3$ is CO—$R^{19}$, CS—$R^{20}$ or $SO_2$—$R^{21}$, $R^4$ is H or $CH_3$, $R^{19}$ is H, $C_1-C_4$-alkyl, $C_2-C_4$-alkenyl, $C_2-C_4$-alkynyl, $C_1-C_4$-alkoxy, $C_1-C_4$-alkylthio, $C_2-C_4$-alkenoxy, $C_2-C_4$-alkynoxy, $C_3-C_6$-cycloalkyl, $C_1-C_4$-alkylamino, di-$(C_1-C_4$-alkyl) amino, N—$C_1-C_2$-alkoxy-N—$C_1-C_2$-alkylamino, where each of the 10 radicals mentioned last is unsubstituted or substituted by one or more radicals from the group consisting of halogen and $C_1-C_4$-alkoxy, or a phenyl or phenoxy radical, which is unsubstituted or substituted by radicals from the group consisting of halogen, $C_1-C_2$-alkyl, $C_1-C_2$-alkoxy, $C_1-C_2$-haloalkyl and $C_1-C_2$-haloalkoxy, $R^{20}$ is a radical analogous to $R^{19}$, and $R^{21}$ is $C_1-C_3$-alkyl, $C_1-C_3$-haloalkyl or $C_1-C_3$-alkoxy-$C_1-C_2$-alkyl.

Preferred compounds of the formula (I) according to the invention are those in which the group of the formula $NHR^3$ on the phenyl radical is in the para-position to the group $CW^1$—$NR^1R^2$ and in the meta-position to the $SO_2$ group.

Preferred compounds of the formula (I) according to the invention are also those which contain a combination of the abovementioned radicals which are preferred in each case.

The present invention furthermore relates to processes for the preparation of the compounds of the formula (I) according to the invention or of salts thereof, which comprises a) reacting a compound of the formula (II)

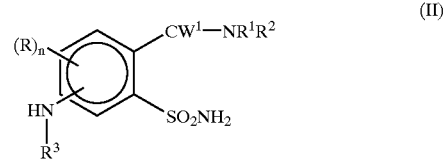

with a heterocyclic carbamate of the formula (III),

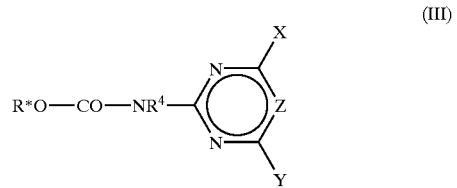

in which R* is unsubstituted or substituted phenyl or $C^1-C^4$-alkyl, or b) reacting a sulfonyl isocyanate of the formula (IV)

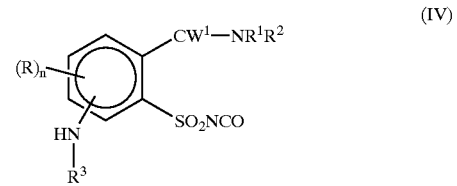

with a heterocyclic amine of the formula (V)

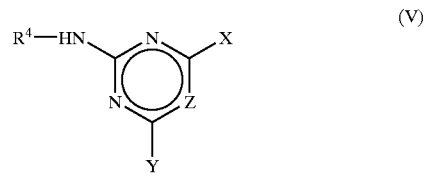

or c) reacting a sulfonyl chloride of the formula (VI)

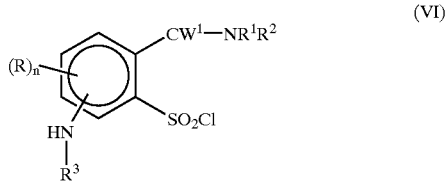

(VI)

with a heterocyclic amine of the above formula (V) in the presence of a cyanate, for example an alkaline metal cyanate, such as sodium cyanate or potassium cyanate, or d) reacting a sulfonamide of the above formula (II) with a (thio)isocyanate of the formula (VII)

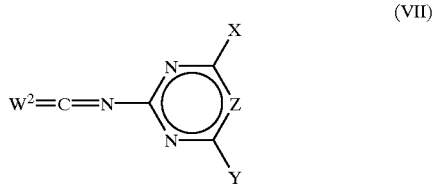

(VII)

in the presence of a suitable base, such as, for example, potassium carbonate or triethylamine, in which, in the above formulae (II) to (VII), the radicals R, $R^1$, $R^2$, $R^3$, $R^4$, $W^1$, $W^2$, X, Y and Z and the index n are as defined in formula (I), and where compounds of the formula (I) in which $W^2$ is an oxygen atom are first obtained in variants a)–c).

The sulfonamides (II), the sulfonyl isocyanates (IV) and the sulfonyl chlorides (VI) are novel compounds. The invention likewise relates to these compounds and to their preparation.

The reaction of the compounds of the formula (II) and (III) is preferably carried out under base catalysis in inert solvents, such as, for example, methylene chloride, acetonitrile, dioxane or tetrahydrofuran, at temperatures from –10° C. up to the boiling point of the particular solvent. Bases which are used here are, for example, organic amine bases, such as 1,8-diazabicyclo[5.4.0]-undec-7-ene (DBU), in particular in the case where R*=(substituted) phenyl (cf. EP-A-44807), or trimethyl- or triethylaluminium, the latter in particular in the case where R*=alkyl (cf. EP-A-166 516).

The compounds of the formula (II) are obtained, for example, from N-(t-butyl)-sulfonamides of the formulae (VIII), (IX) and (X) (cf. formula VIII*, Z*=$R^3$NH—)

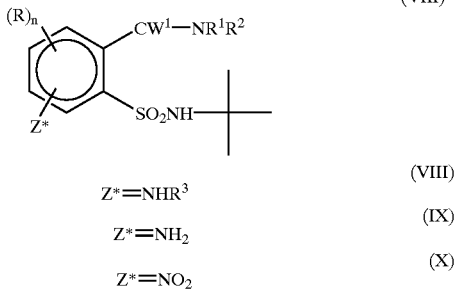

(VIII)*

Z*=NHR³ (VIII)

Z*=NH₂ (IX)

Z*=NO₂ (X)

Starting from compounds of the formula (VIII) in which R, n, $R^1$, $R^2$, $R^3$ and $W^1$ are as defined in formula (I), compounds of the formula (II) are obtained by reaction with a strong acid. Possible strong acids are, for example, mineral acids, such as $H_2SO_4$ or HCl, or strong organic acids, such as trifluoroacetic acid. The t-butyl group is split off at temperatures of from –20° C. to the particular reflux temperature of the reaction mixture, preferably at from 0° C. to 40° C. The reaction can be carried out in bulk or also in a solvent, such as, for example, methylene chloride or chloroform.

The compounds of the formula (VIII) are obtained, for example, from the aniline derivatives of the formula (IX) (cf. formula (VIII), R*=$NH_2$) by reaction with suitable electrophiles, such as, for example, acid chlorides, acid anhydrides, isocyanates, thioisocyanates, sulfonyl chlorides or amidosulfonyl chlorides (in this context, cf.: A. L. J. Beckniter in J. Zabicky, "The Chemistry of Amides", pages 73–185, Interscience, New York, 1970; E. J. Corey et al., Tetrahedron Lett. 1978, 1051; H. J. Saunders, R. J. Slocombe, Chem. Rev. 43, 203 (1948); S. Ozaki, Chem. Rev. 72, 457, 469 (1972); G. Zölβ, Arzneim.-Forsch. 33, 2 (1983); Houben-Weyl-Hagemann, "Methoden der organischen Chemie" (Methods of organic chemistry), 4th edition, volume E4, page 485 et seq., Thieme Verlag Stuttgart, 1983; J. Golinsky, M. Mohasza, Synthesis 1978, 823; Houben-Weyl-Müller "Methoden der organischen Chemie" (Methods of organic chemistry), 4th edition, volume IX, pages 338–400 and 605–622, Thieme Verlag Stuttgart, 1955; Houben-Weyl-Klarmann, "Methoden der organischen Chemie" (Methods of organic chemistry), 4th edition, volume E 11/2, pages 1020–22, Thieme Verlag Stuttgart, 1985; S. Krishnamurthey, Tetrahedron Lett. 23, 3315 (1982).).

The anilines (IX) mentioned are obtained by processes which are known from the literature, for example by reduction of the nitro groups from the compounds (X) (cf. formula (VIII), Z*=$NO_2$), for example by catalytic hydrogenation or by reduction with iron in an acetic acid medium (in this context, cf.: H. Berrie, G. T. Neuhold, F. S. Spring, J. Chem. Soc. 1952, 2042; M. Freifelder, "Catalytic Hydrogenation in Organic Synthesis: Procedures and Commentary", J. Wiley and Sons, New York (1978), chapter 5).

The compounds of the formula (X) can be obtained by amidation, starting from the benzoates of the formula (XI):

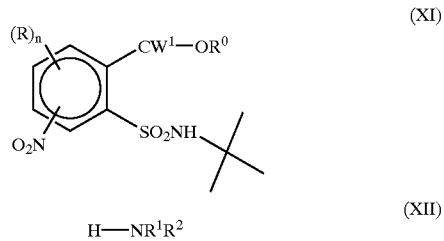

(XI)

(XII)

H—NR¹R²

The amide formation is carried out by reacting the benzoates (XI) (R°=alkyl) with the amines of the formula (XII). The compounds of the formula (XI) and (XII) are starting materials which are known from the literature or commercially obtainable (cf., for example, German Patent Application P 42 36 902.9), or the compounds can be prepared analogously to generally known processes.

The amides of the formulae (VIII), (IX) and (X) are novel compounds. The invention likewise relates to these compounds and to their preparation.

The following synthesis sequence, which is explained below using the example of compounds where n=0, offers an alternative access to compounds (XI) ($W^1$=0). Starting from 2-amino-nitrobenzoic acids (XIII), for example 2-amino-4-nitrobenzoic acid (XIIIa), the corresponding benzoic acid esters (XIV) (R°=alkyl) are obtained by conventional esterification with the corresponding alcohols (R°OH) and a suitable acid, such as, for example, $H_2SO_4$.

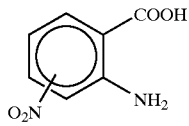
(XIII)

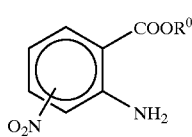
(XIV)

Diazotization of the amino group and subsequent reaction with $SO_2/CuCl_2$ gives the sulfonyl chloride (XV) (analogously to Meerwein, Chem. Ber. 90 (1957) 841–852).

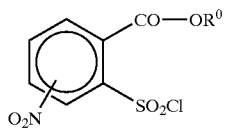
(XV)

Ammonolysis of compounds of the formula (XV) with t-butylamine leads to the sulfonamides of the formula (XI).

The carbamates of the formula (III) required for the reaction of the compounds (II) according to variant a) are known from the literature or can be prepared analogously to known processes (cf. EP-A-70 804 or U.S. Pat. No. 4,480, 101).

The phenylsulfonyl isocyanates of the formula (IV) can be prepared, for example, analogously to the processes from EP-A-184 385 from compounds of the formula (II), for example with phosgene.

The reaction of the compounds (IV) with the aminoheterocyclic compounds of the formula (V) is preferably carried out in inert, aprotic solvents, such as, for example, dioxane, acetonitrile or tetrahydrofuran, at temperatures of between 0° C. and the boiling point of the solvent.

The reaction of the sulfonyl chlorides (VI) with the amino-heterocyclic compounds of the formula (V) and cyanates, such as sodium cyanate and potassium cyanate, is carried out, for example, in aprotic solvents, such as, for example, acetonitrile, if appropriate in the presence of bases, for example 0.5 to 2 equivalents of base, or in basic aprotic solvents, at temperatures between −10° C. and 100° C., preferably −10° C. and 60° C., in particular at from 15° C. to 40° C. Possible bases or basic aprotic solvents are, for example, pyridine, picoline or lutidine or a mixture of these (cf. U.S. Pat. No. 5,157,119).

The (thio)isocyanates of the formula (VII) are obtainable by processes known from the literature (EP-A-232067, EP-A-166516). The reaction of the (thio)isocyanates (VII) with compounds (II) is carried out at from −10° C. to 100° C., preferably from 20 to 100° C., in an inert aprotic solvent, such as, for example, acetone or acetonitrile, in the presence of a suitable base, for example $N(C_2H_5)_3$ or $K_2CO_3$.

The salts of the compounds of the formula (I) are preferably prepared in inert solvents, such as, for example, water, methanol, acetone, methylene chloride, tetrahydrofuran, toluene or heptane, at temperatures of from 0 to 100° C. Suitable bases for the preparation of the salts according to the invention are, for example, alkali metal carbonates, such as potassium carbonate, alkali metal and alkaline earth metal hydroxides, such as NaOH, KOH and $Ca(OH)_2$, ammonia or a suitable amine base, such as triethylamine or ethanolamine. Suitable acids for the salt formation are, for example, HCl, HBr, $H_2SO_4$ or $HNO_3$.

The "inert solvents" refer red to in the above process variants in each case mean solvents which are inert under the particular reaction conditions but are not required to be inert under any reaction conditions.

The compounds of the formula (I) according to the invention or salts thereof have an excellent herbicidal activity against a broad spectrum of economically important mono- and dicotyledon harmful plants. Perennial weeds which are difficult to combat and shoot from rhizomes, root stock or other permanent organs are also readily affected by the active compounds. it is irrelevant here whether the substances are applied prior to sowing, pre-emergence or post-emergence. Examples of some representatives of the mono- and dicotyledon weed flora which can be controlled by the compounds according to the invention may be mentioned specifically, without naming of these being intended as a limitation to particular species.

On the part of monocotyledon species of weeds, for example, Avena, Lolium, Alopecurus, Phalaris, Echinochloa, Digitaria, Setaria and Cyperus species from the annual group and on the part of the perennial species Agropyron, Cynodon, Imperata and Sorghum and also persistent species of Cyperus are readily affected. In the case of dicotyledon species of weed, the action spectrum extends to species such as, for example, Galium, Viola, Veronica, Lamium, Stellaria, Amaranthus, Sinapis, Ipomoea, Matricaria, Abutilon and Sida on the annual side and Convolvulus, Cirsium, Rumex and Artemisia among the perennial weeds.

Weeds which occur under the specific growing conditions in rice, such as, for example, Sagittaria, Alisma, Eleocharis, Scirpus and Cyperus, are also combated outstandingly by the active compounds according to the invention.

If the compounds according to the invention are applied to the soil surface before germination, either the emergence of the weed seedlings is prevented completely, or the weeds grow to the cotyledon stage but then stop growing, and finally die completely after three to four weeks have elapsed.

When the active compounds are applied to the green parts of plants by the post-emergence method, a drastic stop in growth likewise occurs very rapidly after the treatment, and the weed plants remain in the growth stage existing at the time of application or die completely after a certain period, so that weed competition which is harmful to crop plants is eliminated very early and lastingly in this manner.

Although the compounds according to the invention have an excellent herbicidal activity against mono- and dicotyledon weeds, crop plants of economically important crops, such as, for example, wheat, barley, rye, rice, maize, sugar beet, cotton and soya, are damaged only insignificantly or not at all. For these reasons, the present compounds are particularly suitable for selectively combating undesirable plant growth in agricultural crops of useful plants.

The substances according to the invention furthermore have outstanding growth regulatory properties in crop plants. They intervene by regulation in the endogenous plant metabolism and can therefore be used for specific influencing of plant contents and for facilitating harvesting, for example by inducing desiccation and compressed growth. They are furthermore also suitable for general control and inhibition of undesirable vegetative growth, without thereby killing the plants. Inhibition of vegetative growth plays a major role in many mono- and dicotyledon crops, since lodging can thereby be reduced or prevented completely.

The compounds according to the invention can be used in the form of wettable powders, emulsifiable concentrates, sprayable solutions, dusts or granules in the usual formulations. The invention therefore also relates to herbicidal and plant growth regulating compositions which comprise compounds of the formula (I) or salts thereof.

The compounds of the formula (I) or salts thereof can be formulated in various ways, depending on the biological and/or chemico-physical parameters which exist. Suitable formulation possibilities are, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), dressing compositions, granules for application by scattering and soil application, granules (GR) in the form of microgranules, spray granules, absorption granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" (Chemical Technology), volume 7, C. Hauser Verlag Munich, 4th edition, 1986, Wade van Valkenburg, "Pesticide Formulations", Marcel Dekker, N.Y., 1973; K. Martens, "Spray Drying" Handbook, 3rd Edition 1979, G. Goodwin Ltd. London.

The necessary formulation auxiliaries, such as inert materials, surfactants, solvents and other additives, are likewise known and are described for example, in: Watkins, "Handbook of Insecticide Dust Diluents and Carriers", 2nd Edition, Darland Books, Caldwell N.J., H.v. Olphen, "Introduction to Clay Colloid Chemistry"; 2nd Edition, J. Wiley & Sons, N.Y.; C. Marsden, "Solvents Guide"; 2nd Edition, Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" (Surface-active ethylene oxide adducts), Wiss. Verlagsgesell., Stuttgart 1976; Winnacker-Küchler, "Chemische Technologie" (Chemical Technology), volume 7, C. Hauser Verlag Munich, 4th Edition, 1986.

Combinations with other substances having a pesticidal action, such as, for example, insecticides, acaricides, other herbicides, fungicides, safeners, fertilizers and/or growth regulators, can also be prepared on the basis of these formulations, for example in the form of a finished formulation or as a tank mix.

Wettable powders are preparations which are uniformly dispersible in water and, in addition to the active compound, as well as a diluent or inert substance, also comprise surfactants of an ionic and/or nonionic nature (wetting agents, dispersing agents), for example polyoxyethylated alkylphenols, polyoxyethylated fatty alcohols, polyoxyethylated fatty amines, fatty alcohol polyglycolether-sulfates, alkane sulfonates, alkylbenzenesulfonates, the sodium salt of ligninsulfonic acid, the sodium salt of 2,2'-dinaphthylmethane-6,6'-disulfonic acid, the sodium salt of dibutylnaphthalene-sulfonate or also the sodium salt of oleoylmethyltaurine. To prepare the wettable powders, for example, the herbicidal active compounds are finely ground in customary apparatuses, such as hammer mills, blast mills and air jet mills, and mixed with the formulation auxiliaries at the same time or subsequently.

Emulsifiable concentrates are prepared by dissolving the active compound in an organic solvent, for example butanol, cyclohexanone, dimethylformamide, xylene or else higher-boiling aromatics or hydrocarbons or mixtures of the organic solvents, with addition of one or more surfactants of ionic and/or nonionic nature (emulsifiers). Emulsifiers which can be used are, for example: calcium salts of alkylarylsulfonic acids, such as Ca dodecylbenzenesulfonate, or nonionic emulsifiers, such as fatty acid polyglycol esters, alkylarylpolyglycol ethers, fatty alcohol polyglycol ethers, propyleneoxide/ethyleneoxide condensation products, alkylpolyethers, sorbitan esters, such as, for example, sorbitan fatty acid esters, or polyoxyethylenesorbitan esters, such as, for example, polyoxyethylenesorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet grinding by means of commercially available bead mills and if appropriate addition of surfactants, such as have already been listed above, for example, for the other types of formulation.

Emulsions, for example oil-in-water emulsions (EW), can be prepared, for example, by means of stirrers, colloid mills and/or static mixers using aqueous organic solvents and if appropriate surfactants, such as have already been listed above, for example, for the other types of formulation.

Granules can be fed either by spraying the active compound onto adsorbent, granular inert material or by application of active compound concentrates by means of adhesives, for example polyvinyl alcohol, the sodium salt of polyacrylic acid or mineral oils, to the surface of carriers, such as sand, kaolinites, or granular inert material. Suitable active compounds can also be granulated in the manner customary for the preparation of fertilizer granules—if desired as a mixture with fertilizers.

Water-dispersible granules are as a rule prepared by the customary processes, such as spray drying, fluidized bed granulation, plate granulation, mixing with high-speed mixers and extrusion without a solid inert material.

The agrochemical formulations as a rule comprise 0.1 to 99% by weight, in particular 0.1 to 95% by weight, of active compound of the formula (I) or salts thereof.

In wettable powders, the active compound concentration is, for example, about 10 to 90% by weight, the remainder to 100% by weight consisting of customary formulation constituents. In emulsifiable concentrates, the active compound concentration can be, for example, 1 to 90, preferably 5 to 80% by weight. Dust-like formulations comprise 1 to 30, preferably usually 5 to 20% by weight of active compound, and sprayable solutions comprise, for example, 0.05 to 80, preferably 2 to 50% by weight of active compound. In water-dispersible granules, the active compound content depends partly on whether the active compound is in liquid or solid form and which granulating auxiliaries, fillers and the like are used. In the case of granules which are dispersible in water, the content of active compound is, for example, between 1 and 95% by weight, preferably between 10 and 80% by weight.

In addition, the active compound formulations mentioned comprise, where appropriate, the particular customary adhesives, wetting agents, dispersing agents, emulsifiers, penetration agents, preservatives, antifrost agents and solvents, fillers, carriers and dyestuffs, defoamers, evaporation inhibitors and agents which influence the pH and the viscosity.

Combination partners which can be employed for the active compounds according to the invention in mixture formulations or in a tank mix are, for example, known active compounds such as are described, for example, in Weed Research 26, 441–445 (1986), or "The Pesticide Manual", 9th edition, The British Crop Protection Council, 1990/91, Bracknell, England, and literature cited therein. The following active compounds are to be mentioned, for example, as herbicides which are known from the literature and can be combined with compounds of the formula (I) (Note: The compounds are designated either with their "common name" according to the International organization for Standardization (ISO) or by their chemical name, if appropriate together with a customary code number): acetochlor; aciflurofen; aclonifen; AKH 7088, i.e. [[[1-[5-[2-chloro-4-(trifluoromethyl)-phenoxy]-2-nitrophenyl]-2-methoxyethylidene]-amino]-oxy]-acetic acid and acetic acid methyl ester; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenylacetamide; CDEC, i.e. diethyldithiocarbamic acid-2-chloroallylester; CGA 184927, i.e. 2-[4-[(5-chloro-3-fluoro-2-pyridinyl)-oxy]-phenoxy]-propanoic acid and 2-propynyl ester; chlomethoxyfen; chloramben; chlorazifop-butyl, pirifenop-butyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmedipham; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone, clomazon; dimethipin; dimetrasulfuron, cinosulfuron; dinitramine; dinoseb; dinoterb; diphenamid; dipropetryn; diquat; dithiopyr; diuron; DNOC; eglinazine-ethyl; EL 177, i.e. 5-cyano-1(1,1-dimethylethyl)-N-methyl-3H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]-phenyl]-ethanesulfonamide; F6285, i.e. 1-[5-(N-methylsulfonyl)-amino-2,4-dichlorophenyl]-3-methyl-4-difluoromethyl-1,2,4-triazol-5-one; fenoprop; fenoxan, s. clomazon; fenoxaprop-ethyl; fenuron; flamprop-methyl; flazasulfuron; fluazifop and ester derivatives thereof; fluchloralin; flumetsulam; N-[2,6-difluorophenyl]-5-methyl-(1,2,4-triazolo-[1,5a]pyrimidine-2-sulfonamide; flumeturon; flumipropyn; fluorodifen; fluoroglycofenethyl; fluridone; flurochloridone; fluroxypyr; flurtamone; fomesafen; fosamine; furyloxyfen; glufosinate; glyphosate; halosaten; haloxyfop and ester derivatives thereof; hexazinone; Hw 52, i.e. N-(2,3-dichlorophenyl)-4-ethoxymethoxy) benzamide; imazamethabenz-methyl; imazapyr; imazaquin; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopham; phenmedipham; picloram; piperophos, piributicarb; pirifenop-butyl; pretilachlor; primisulfuronmethyl; procyazine; prodiamine; profluralin; proglinazine-ethyl; prometon; prometryn; propachlor; propanil, propaquizafop and ester derivatives thereof; propazine, propham, propyzamide; prosulfalin, prosulfocarb; prynachlor; pyrazolinate, pyrazon; pyrazosulfuronethyl; pyrazoxyfen; pyridate; quinclorac; quinmerac; quinofop and ester derivatives thereof, quizalofop and ester derivatives thereof; quazalofop-ethyl; quizalofop-p-tefuryl; renriduron; dymron; S 275 i.e. 2-[4-chloro-2-fluoro-5-(2-propynyloxy)-phenyl]4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoromethyl)-phenoxy]-2-naphthyl]-oxy]-propanoic acid and its methyl ester; sulfometuron-methyl; sulfazuron; flazasulfuron; TCA; tebutam; tebuthiuron; terbacil; terbucarb; terbuchlor; terbumeton; terbuthylazine; terbutryn; TFH 450, i.e. N,N-diethyl-3-[(2-ethyl-6-methylphenyl)-sulfonyl]-1H-1,2,4-triazole-1-carboxamide; thiazafluron, thifensulfuron-methyl; thiobencarb; tiocarbazil; tralkoxydim; tri-allate; triasulfuron; triazofenamide; tribenuron-methyl; triclopyr; tridiphane; trietazine; trifluralin; trimeturon; vernolate; WL 110547, i.e. 5-phenoxy-1-[3-(trifluoromethyl)-phenyl]-1H-tetrazole.

For use, the formulations present in the commercially available form are diluted in the customary manner, if appropriate, for example by means of water in the case of wettable powders, emulsifiable concentrates, dispersions and water-dispersible granules, and then applied to the plants, parts of plants, or soil on which the plants are standing or in which they are growing or are present as seed and which is used agriculturally or industrially. Dust-like formulations, soil granules and granules for scattering as well as sprayable solutions are usually not additionally diluted with further inert substances before use.

The required amount of compounds of the formula (I) to be applied varies according to the external conditions, such as temperature, humidity and nature of herbicide used, inter alia. It can vary within wide limits, for example between 0.001 and 10.0 kg/ha or more of active substance, but is preferably between 0.005 and 5 kg/ha.

A. CHEMICAL EXAMPLES a) Methyl 2-amino-4-nitro-benzoate

A mixture of 118.8 g of 2-amino-4-nitro-benzoic acid, 1000 ml of methanol and 120 ml of concentrated sulfuric acid is heated at the boiling point for 16 hours. The mixture is concentrated under reduced pressure, the residue is taken up in ethyl acetate and the mixture is washed with saturated $NaHCO_3$ solution. After drying over $Na_2SO_4$, the organic phase is concentrated. 114.2 g (89%) of methyl 2-amino-4-nitro-benzoate are thus obtained with a melting point (m.p.) of 156–158° C.

b) Methyl 2-chlorosulfonyl-4-nitro-benzoate

A solution of 122.3 g of sodium nitrite in 180 ml of water is added dropwise to a suspension of 1300 ml of glacial acetic acid, 516 ml of concentrated hydrochloric acid and 441.7 g (1.689 mol) of methyl 2-amino-4-nitro-benzoate (Example a) at a temperature of between 13 and 15° C. After this reaction mixture has been stirred for 30 minutes, it is added dropwise to a solution, saturated with $SO_2$, of 17 g of copper(II) chloride and 1300 ml of glacial acetic acid at about 26° C. When the evolution of gas has ended, the mixture is poured onto ice-water and the sulfonyl chloride which has precipitated out is filtered off with suction and washed with water to give, after drying, 354.3 g of methyl 2-chlorosulfonyl-4-nitro-benzoate; m.p.: 88–90° C.

c) N-tert.-butyl-2-methoxycarbonyl-5-nitro-benzenesulfonamide 206 g of tert-butylamine are added dropwise to a solution of 384 g of methyl 2-chlorosulfonyl-4-nitro-benzoate (Example b) in 1500 ml of ethyl acetate at 0° C. The reaction mixture is then allowed to warm up to room temperature and is stirred at this temperature for 1 hour. After washing with dilute hydrochloric acid and water, the organic phase is dried over $MgSO_4$ and concentrated. The residue is extracted by stirring with diisopropyl ether; Yield of sulfonamide: 377.6 g; m.p.: 122–124° C.

d) N-tert.-butyl-2-dimethylaminocarbonyl-5-nitro-benzosulfonamide 115 g of N-tert.-butyl-2-methoxycarbonyl-5-nitrobenzenesulfonamide (Example c) in 1500 ml of methanol are gassed with about 200 g of dimethylamine. The mixture is stirred at about 35° C. for one week. The solution is concentrated under reduced pressure, the residue is taken up in ethyl acetate and the mixture is washed successively with dilute hydrochloric acid, saturated $NaHCO_3$ solution and saturated NaCl solution. After drying over $MgSO_4$, the organic phase is concentrated. 92 g of N-tert.-butyl-2-dimethylaminocarbonyl-5-nitro-benzensulfonamide are obtained: m.p.: 138–141° C.

e) 5-Amino-N-tert.-butyl-2-dimethylaminocarbonylbenzenesulfonamide 23.6 g of zinc powder are added to a suspension of 22.0 g of N-tert.-butyl-2-dimethylaminocarbonyl-5-nitro-benzenesulfonamide (Example d), 18.2 g of ammonium chloride, 70 ml of water and 150 ml of methanol. The mixture is then stirred at 50° C. When the reaction has ended, the solid is filtered off. After the solid has been washed with ethyl acetate, the filtrate is concentrated, the residue is taken up in ethyl acetate and the mixture is washed with water. After drying over $MgSO_4$, the organic phase is concentrated and the residue is washed with diisopropyl ether; yield: 17.5 g; m.p.: 205–208° C.

f) N-tert.-butyl-2-dimethylaminocarbonyl-5-methoxycarbonylaminobenzensulfonamide 0.47 g of methyl chloroformate is added dropwise to a suspension of 1.50 g of 5-amino-N-tert.-butyl-2-dimethylaminocarbonyl-benzenesulfonamide (Example e) and 1.46 g of $NaHCO_3$ in 50 ml of $CH_3CN$ at 0° C. When the reaction has ended, the reaction mixture is taken up in ethyl acetate and the mixture is washed with 1N hydrochloric acid, dried over $MgSO_4$ and concentrated. 1.48 g of N-tert.-butyl-2-dimethylaminocarbonyl-5-methoxycarbonylamino-benzenesulfonamide are thus obtained; m.p.: 184–188° C.

g) N-tert.-butyl-2-dimethylaminocarbonyl-5-formylaminobenzenesulfonamide

A mixture of 0.34 ml of formic acid and 0.70 ml of acetic anhydride is heated at 50° C. for 2 hours, and a solution of 0.85 g of 5-amino-N-tert.-butyl-2-dimethylaminocarbonyl-benzenesulfonamide (Example e) and 3.5 ml of dimethylformamide (DMF) is added. After 4 hours, the mixture is taken up in ethyl acetate and washed successively with dilute hydrochloric acid and saturated $NaHCO_3$ solution. After the mixture has been dried over $MgSO_4$ and the organic phase has been concentrated, 0.88 g of a highly viscous substance, which is used in subsequent reactions without further purification (Example j), is obtained.

h) N-tert.-butyl-2-dimethylaminocarbonyl-5-propionylamino-benzenesulfonamide 0.85 g of 5-amino-N-tert.-butyl-2-dimethylaminocarbonyl-benzenesulfonamide (Example e) is dissolved in 3.5 ml of DMF at 0° C., and 0.28 g of propionyl chloride and 0.50 ml of triethylamine are added. After the mixture has been stirred at 5° C. for 1 hour, it is taken up in ethyl acetate and washed successively with dilute hydrochloric acid and water. After the mixture has been dried over $MgSO_4$ and the organic phase has been concentrated, 0.60 g of a highly viscous substance, which is employed in subsequent reactions without further purification (Example k), is obtained.

i) 2Dimethylaminocarbonyl-5-methoxycarbonylamino-benzenesulfonamide 1.48 g of N-tert.-butyl-2-dimethylaminocarbonyl-5-methoxycarbonylamino-benzenesulfonamide (Example f) are stirred in 25 ml of trifluoroacetic acid for 18 hours. After the acid has been distilled off, the residue is suspended in toluene. Renewed concentration gives 1.40 g of the sulfonamide; m.p.: 75–77° C.

j) 2-Dimethylaminocarbonyl-5-formylamino-benzenesulfonamide 0.85 g of N-tert.-butyl-2-dimethylamino-carbonyl-5-formylamino-benzenesulfonamide (Example g) is reacted with 10 ml of trifluoroacetic acid analogously to Example i. 0.88 g of a highly viscous mass, which is employed in the reaction described under Example m without further purification, is thus obtained.

k) 2-Dimethylaminocarbonyl-5-propionylamino-benzensulfonamide 0.80 g of N-tert.-butyl-2-dimethylamino-carbonyl-5-propionylamino-benzenesulfonamide is reacted with 10 ml of trifluoroacetic acid analogously to Example 1. 0.80 g of a highly viscous mass, which is employed in the reaction described under Example n) without further purification, is thus obtained.

l) N-[(4,6-dimethoxypyrimidin-2-yl]-aminocarbonyl]-2-dimethyl-aminocarbonyl-5-methoxycarbonylaminobenzenesulfonamide (cf. Example 53 from Table 1)

DBU is added to a suspension of 1.40 g of 2-dimethylaminocarbonyl-5-methoxycarbonylamino-benzenesulfonamide (Example i) and 1.28 g of 4,6-dimethoxy-2-phenoxycarbonylamino-pyrimidine in 30 ml $CH_3CN$ at 0° C. The reaction temperature is then allowed to rise slowly to room temperature. After the solvent has been distilled off, the residue is taken up in water and the mixture is washed with diethyl ether. After the aqueous phase has been acidified with concentrated hydrochloric acid, the sulfonyl urea which has separated out is washed with methanol and diisopropyl ether and then dried. Yield: 1.45 g as a colorless solid of m.p. 181–182° C. (decomposition).

m) N-[4,6-dimethoxypyrimidin-2-yl)-aminocarbonyl]-2-dimethylaminocarbonyl-5-formylamino-benzenesulfonamide (cf. Example 8 from Table 1)

0.88 g of 2-dimethylaminocarbonyl-5-formyl-aminobenzenesulfonamide (Example j) is reacted with 0.89 g of 4,6-dimethoxy-2-phenoxycarbonylaminopyrimidine and 0.98 g of DBU in 10 ml of $CH_3CN$ analogously to Example 1). 0.69 g of the crystalline sulfonylurea is obtained with m.p.: 126–127° C. (decomposition).

n) N-[(4,6-dimethoxypyrimidin-2-yl)-aminocarbonyl]-2-dimethylaminocarbonyl-5-propionylamino-benzenesulfonamide (cf. Example 22 from Table 1)

0.80 g of 2-dimethylaminocarbonyl-5-propionylamino-benzenesulfonamide is reacted with 0.74 g of 4,6-dimethoxy-2-phenoxycarbonylamino-pyrimidine and 0.82 g of DBU in 10 ml of $CH_3CN$ analogously to Example 1). 0.68 g of the crystalline sulfonylurea is obtained with m.p.: 135–140° C. (decomposition).

o) N-[(4,6-dimethoxypyrimidin-2-yl)-aminocarbonyl]-2-dimethylaminocarbonyl-5-methoxycarbonylamino-benzenesulfonamide sodium salt
(cf. Example 21 from Table 2)

1.85 ml of 1N sodium hydroxide solution are added to a mixture of 0.93 g of N-[(4-dimethoxypyrimidin-2-yl)-aminocarbonyl]-2-dimethylaminocarbonyl-5-methoxycarbonyl-amino-benzenesulfonamide in 20 ml of $CH_3CN$. After a clear solution has formed, the mixture is concentrated under reduced pressure. The residue is stirred with a little diisopropyl ether. 0.82 g of the salt is thus obtained with m.p.: 187–191° C. (decomposition).

p) N-[(4,6-dimethoxypyrimidin-2-yl)-aminocarbonyl]-2-dimethylaminocarbonyl-5-formylamino-benzenesulfonamide sodium salt
(cf. Example 1 from Table 2)

0.30 g of N-[(4,6-dimethoxypyrimidin-2-yl)-aminocarbonyl]-2-dimethylaminocarbonyl-5-formylamino-benzenesulfonamide (Example m) and 0.65 ml of 1N sodium hydroxide solution in 4 ml of methanol and 4 ml of $CH_2Cl_2$ are reacted analogously to Example o). 0.32 g of the salt is obtained; m.p.: 205° C. (decomposition).

q) N-[(4,6-dimethoxypyrimidin-2-yl)-aminocarbonyl]-2-dimethylaminocarbonyl-5-propionylamino-benzenesulfonamide sodium salt
(cf. Example 12 from Table 2)

0.30 g of N-[(4,6-dimethoxypyrimidin-2-yl)-aminocarbonyl]-2-dimethylaminocarbonyl-5-propionylamino-benzenesulfonamide (Example n) and 0.60 ml of 1N sodium hydroxide solution in 4 ml of methanol and 4 ml of $CH_2Cl_2$ are reacted analogously to Example o). 0.31 g of the salt is thus obtained; m.p.: 212° C. (decomposition).

The compounds described in the following Table 1 are obtained according to or analogously to the above examples l) to n); the compounds described in the following Table 2 are obtained according to or analogously to the above Examples o) to q).

Abbreviations

Mp.=Melting point
Et=Ethyl
Me=Methyl
Pr=$^n$pr=n-Propyl
$^i$Pr=Isopropyl
$^c$Pr=Cyclopropyl
Bu=$^n$Bu=n-Butyl
$^i$Bu=Isobutyl
$^t$Bu=t-Butyl
Ph=Phenyl

TABLE 1

Compounds of the formula (Ia)

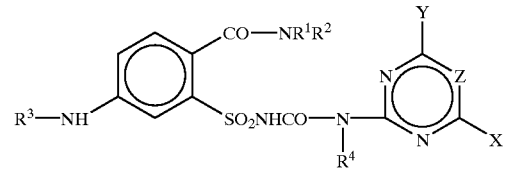

(Ia)

| No. | $R^1$ | $R^2$ | $R^3$ | $R^4$ | X | Y | Z | Mp. [° C.] |
|---|---|---|---|---|---|---|---|---|
| 1 | H | H | $COCH_3$ | H | OMe | OMe | CH | |
| 2 | H | H | CO—H | H | OMe | OMe | CH | |
| 3 | " | " | COOMe | " | " | " | " | |
| 4 | " | Me | $COCH_3$ | " | " | " | " | |
| 5 | " | " | CO—H | " | " | " | " | |
| 6 | " | " | COOMe | " | " | " | " | |
| 7 | " | " | $COCF_3$ | " | " | " | " | |
| 8 | Me | Me | CO—H | " | " | " | " | 126–127 (Decomp.) |
| 9 | " | " | " | " | " | Me | " | |
| 10 | " | " | " | " | " | Cl | " | |
| 11 | " | " | " | " | Me | Me | " | |
| 12 | " | " | " | " | Me | OMe | N | |
| 13 | " | " | " | " | OMe | OMe | N | |
| 14 | " | " | " | " | $NMe_2$ | $OCH_2CF_3$ | N | |
| 15 | " | " | CO—$CH_3$ | " | OMe | OMe | CH | 182–184 (Decomp.) |
| 16 | " | " | " | " | " | Cl | " | |
| 17 | " | " | " | " | " | Me | " | |
| 18 | " | " | " | " | Me | " | " | |
| 19 | Me | Me | CO—$CH_3$ | H | OMe | OMe | N | |
| 20 | " | " | " | " | Me | OMe | " | |
| 21 | " | " | " | " | $NMe_2$ | $OCH_2CF_3$ | " | |
| 22 | " | " | $COCH_2CH_3$ | " | OMe | OMe | CH | 135–140 (Decomp.) |
| 23 | " | " | " | " | OMe | Cl | " | |
| 24 | " | " | CO—$CH_2CH_3$ | " | OMe | Me | N | |

TABLE 1-continued

Compounds of the formula (Ia)

(Ia)

| No. | $R^1$ | $R^2$ | $R^3$ | $R^4$ | X | Y | Z | Mp. [°C.] |
|---|---|---|---|---|---|---|---|---|
| 25 | Me | Me | CO-$^i$Pr | H | OMe | OMe | CH | 145–149 (Decomp.) |
| 26 | " | " | " | " | " | Cl | " | |
| 27 | " | " | " | " | " | Me | " | |
| 28 | " | " | " | " | Me | " | " | |
| 29 | " | " | " | " | OMe | " | N | |
| 30 | " | " | CO-$^t$Bu | " | " | OMe | CH | 202 (Decomp.) |
| 31 | " | " | CO-$^n$Pr | " | " | " | " | |
| 32 | " | " | CO-$^n$Bu | " | " | " | " | |
| 33 | " | " | CO-n-C$_5$H$_{11}$ | " | " | " | " | |
| 34 | " | " | CO—CH$_2$Cl | " | " | " | " | |
| 35 | " | " | " | " | " | Cl | " | |
| 35 | " | " | CO—CHCl$_2$ | " | " | OMe | " | |
| 37 | " | " | CO—CCl$_3$ | " | " | " | " | |
| 38 | " | " | CO—CH$_2$Br | " | " | " | " | |
| 39 | " | " | COCF$_3$ | " | " | " | " | |
| 40 | Me | Me | COCF$_3$ | H | OMe | Me | " | 203 (Decomp.) |
| 41 | " | " | " | " | " | Cl | " | |
| 42 | Me | Me | COCF$_3$ | H | Me | Me | CH | |
| 43 | " | " | " | " | OMe | " | N | |
| 44 | " | " | " | " | " | OMe | N | |
| 45 | " | " | " | " | OCH$_2$CF$_3$ | NMe$_2$ | N | |
| 46 | " | " | COCH$_2$OCH$_3$ | " | OMe | OMe | CH | |
| 47 | " | " | CO—Ph | " | " | " | " | |
| 48 | " | " | CO—(2-furyl) | " | " | " | " | |
| 49 | " | " | CO—(2-thienyl) | " | " | " | " | |
| 50 | Me | Me | CO—CN=CH$_2$ | H | OMe | OMe | CH |
| 51 | " | " | CO—C≡CH | " | " | " | " | |
| 52 | " | " | COCCl=CCl$_2$ | " | " | " | " | |
| 53 | " | " | COOMe | " | " | " | " | 181–182 (Decomp.) |
| 54 | " | " | " | " | " | Me | " | |
| 55 | " | " | " | " | " | Cl | " | 170–172 (Decomp.) |
| 56 | " | " | " | " | Me | Me | " | |
| 57 | " | " | " | " | OMe | OMe | N | |
| 58 | " | " | " | " | OMe | Me | N | 138–139 (Decomp.) |
| 59 | Me | Me | COOEt | H | OMe | OMe | CH | 138 (Decomp.) |
| 60 | " | " | " | " | " | Me | " | |
| 61 | " | " | " | " | " | Cl | " | |
| 62 | Me | Me | COOEt | H | Me | Me | CH | |
| 63 | " | " | " | " | OMe | Me | N | |
| 64 | Me | Me | COO$^i$Pr | H | OMe | OMe | CH | |
| 65 | " | " | COOCH$_2$CH$_2$Cl | " | " | " | " | 154–155 (Decomp.) |
| 66 | " | " | " | " | OMe | Cl | " | |
| 67 | " | " | " | " | " | Me | " | |
| 68 | " | " | CO$_2$CH$_2$CH$_2$Br | " | " | OMe | " | |
| 69 | " | " | CO$_2$CH$_2$CCl$_3$ | " | " | " | " | |
| 70 | " | " | CO—NH$_2$ | " | " | " | " | |
| 71 | " | " | CO—NHMe | " | " | " | " | |

TABLE 1-continued

Compounds of the formula (Ia)

(Ia)

$$R^3-NH-\text{C}_6H_3(CO-NR^1R^2)(SO_2NHCO-N(R^4)-\text{pyrimidine}(X,Y,Z))$$

| No. | $R^1$ | $R^2$ | $R^3$ | $R^4$ | X | Y | Z | Mp. [°C.] |
|---|---|---|---|---|---|---|---|---|
| 72 | " | " | CONHEt | " | " | " | " | 144 (Decomp.) |
| 73 | " | " | CONMe$_2$ | " | " | " | " | |
| 74 | " | " | CONEt$_2$ | " | " | " | " | |
| 75 | " | " | CO—N(Me)—OMe | " | " | " | " | |
| 76 | Me | Me | CS—NHMe | H | OMe | OMe | CH | |
| 77 | " | " | SO$_2$CH$_3$ | " | " | " | " | 190–191 (Decomp.) |
| 78 | " | " | " | " | " | Cl | " | |
| 79 | " | " | " | " | Me | Me | " | |
| 80 | " | " | " | " | Me | OMe | N | |
| 81 | " | " | SO$_2$Et | " | " | " | " | |
| 82 | Me | Me | SO$_2$Et | H | OMe | OMe | CH | |
| 83 | " | " | " | " | " | Cl | " | |
| 84 | " | " | " | " | Me | Me | " | |
| 85 | " | " | SO$_2$CH$_2$Cl | " | OMe | OMe | CH | |
| 86 | Me | Me | SO$_2$CH$_2$F | H | OMe | OMe | CH | |
| 87 | " | " | SO$_2$NHMe | " | " | " | " | 128–129 (Decomp.) |
| 88 | " | " | SO$_2$NMe$_2$ | " | " | " | " | |
| 89 | Et | Et | CO—H | " | " | " | " | 64–67 |
| 90 | Et | Et | CO—CH$_3$ | H | OMe | OMe | CH | 195–197 (Decomp.) |
| 91 | " | " | COOMe | " | " | " | " | |
| 92 | —(CH$_2$)$_4$— | | CO—H | " | " | " | " | |
| 93 | " | | CO—CH$_3$ | " | " | " | " | |
| 94 | " | | COOMe | " | " | " | " | |
| 95 | —O—(CH$_2$)$_3$— | | CO—H | " | " | " | " | |
| 96 | " | | CO—CH$_3$ | " | " | " | " | |
| 97 | " | | COOCH$_3$ | " | " | " | " | |
| 98 | —O—(CH$_2$)$_4$— | | CO—H | " | " | " | " | |
| 99 | " | | CO—CH$_3$ | " | " | " | " | |
| 100 | " | | COOMe | " | " | " | " | |
| 101 | —(CH$_2$)$_2$—O—(CH$_2$)$_2$— | | CO—H | H | OMe | OMe | CH | |
| 102 | " | | CO—CH$_3$ | " | " | " | " | |
| 103 | " | | CO—CH$_2$CH$_3$ | " | " | " | " | |
| 104 | OMe | Me | CO—CH$_3$ | " | " | " | " | |
| 105 | " | " | COOMe | " | " | " | " | |
| 106 | Me | Me | CO—H | Me | " | " | " | |
| 107 | Me | Me | CO—CH$_3$ | Me | OMe | OMe | CH | |
| 108 | " | " | CO—CH$_2$CH$_3$ | " | " | " | " | |
| 109 | " | " | COOMe | " | " | " | " | |
| 110 | " | " | COCF$_3$ | " | " | " | " | |
| 111 | H | Ph | COCH$_3$ | H | OMe | OMe | CH | |
| 112 | " | " | COOCH$_3$ | " | " | " | " | |
| 113 | Me | " | " | " | " | " | " | |
| 114 | Me | Me | CO—Et | " | Me | Me | CH | |
| 115 | " | " | CO-$^c$Pr | " | OMe | OMe | " | 196–197 (Decomp.) |
| 116 | Me | Et | CO—H | " | OMe | OMe | CH | 90 (Decomp.) |
| 117 | Me | $^n$Pr | CO—H | " | " | " | " | |
| 118 | Et | Me | CO—CH$_3$ | " | " | " | " | 192–195 |

TABLE 2

Compounds of the formula (Ib)

[Ib]

| No. | R¹ | R² | R³ | R⁴ | M | X | Y | Z | Mp. (°C.) |
|-----|-----|-----|-----|-----|-----|-----|-----|-----|-----|
| 1 | Me | Me | CO—H | H | Na | OMe | OMe | CH | 205 (Decomp.) |
| 2 | " | " | " | " | K | OMe | OMe | CH | |
| 3 | " | " | " | " | NH₄ | " | " | " | |
| 4 | " | " | " | " | HNEt₃ | " | " | " | |
| 5 | " | " | " | " | Na | OMe | Cl | " | |
| 6 | " | " | " | " | " | OMe | Me | N | |
| 7 | " | " | CO—CH₃ | " | " | " | OMe | CH | 196 (Decomp.) |
| 8 | " | " | " | " | K | " | " | " | |
| 9 | " | " | " | " | Na | " | Cl | " | |
| 10 | " | " | " | " | " | Me | Me | " | |
| 11 | Me | Me | CO—CH₃ | H | Na | OMe | Me | N | |
| 12 | " | " | COCH₂CH₃ | " | " | OMe | OMe | CH | 212 (Decomp.) |
| 13 | " | " | " | " | " | OMe | Cl | CH | |
| 14 | " | " | " | " | " | OMe | Me | N | |
| 15 | " | " | " | " | " | NMe₂ | OCM₂CF₃ | N | |
| 16 | " | " | CO-ⁱPr | " | " | OMe | OMe | CH | 208 (Decomp.) |
| 17 | " | " | COCF₃ | " | " | " | " | " | 198–201 (Decomp.) |
| 18 | " | " | " | " | " | " | Cl | " | |
| 19 | Me | Me | COCF₃ | H | Na | OMe | Me | N | |
| 20 | " | " | COOMe | " | " | " | " | " | 167–170 (Decomp.) |
| 21 | " | " | " | " | " | OMe | OMe | CH | 187–191 (Decomp.) |
| 22 | Me | Me | COOMe | H | Na | OMe | Cl | CH | 267–270 (Decomp.) |
| 23 | " | " | " | " | " | " | Me | " | |
| 24 | " | " | " | " | " | Me | " | " | |
| 25 | " | " | " | " | K | OMe | OMe | " | |
| 26 | " | " | COOEt | " | Na | " | " | " | 194–198 (Decomp.) |
| 27 | " | " | COOⁱPr | " | " | " | " | " | |
| 28 | " | " | CO₂CH₂CH₂Cl | " | " | " | " | " | 159–165 (Decomp.) |
| 29 | " | " | SO₂CH₃ | " | " | " | " | " | 130–134 (Decomp.) |
| 30 | Me | Me | SO₂NHMe | H | Na | OMe | OMe | CH | 187–189 (Decomp.) |
| 31 | " | " | SO₂CH₂Cl | " | " | " | " | " | |
| 32 | " | " | CO-ᶜPr | " | " | " | " | " | 194 (Decomp.) |
| 33 | " | " | CO—NHEt | " | " | " | " | " | 195–198 (Decomp.) |
| 34 | " | " | CO-ᵗBu | " | " | " | " | " | 201 (Decomp.) |
| 35 | " | Et | CO—H | " | " | " | " | " | |
| 36 | " | ⁿPr | CO—H | " | " | " | " | " | |

B. FORMULATION EXAMPLES a) A dust composition is obtained by mixing 10 parts by weight of a compound of the formula (I) and 90 parts by weight of talc, as the inert substance, and comminuting the mixture in an impact mill.
b) A wettable powder which is readily dispersible in water is obtained by mixing 25 parts by weight of a compound of the formula (I), 64 parts by weight of kaolin-containing quartz, as the inert substance, 10 parts by weight of the potassium salt of lignin-sulfonic acid and 1 part by weight of the sodium salt of oleoylmethyltaurine, as the wetting and dispersing agent, and grinding the mixture in a pinned disk mill.
c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 mol of ethylene oxide) and 71 parts by weight of paraffinic mineral oil (boiling range, for example, about 255 to above 277° C.)

and grinding the mixture to a fineness of less than 5 microns in a frictional bead mill.
d) An emulsifiable concentrate is obtained from 15 parts by weight of a compound of the formula (1), 75 parts by weight of cyclohexanone, as the solvent, and 10 parts by weight of oxyethylated nonylphenol, as the emulsifier.
e) Water-dispersible granules are obtained by mixing
  75 parts by weight of a compound of the formula (I),
  10 parts by weight of the calcium salt of ligninsulfonic acid,
  5 parts by weight of sodium lauryl sulfate,
  3 parts by weight of polyvinyl alcohol and
  7 parts by weight of kaolin,
  grinding the mixture on a pinned disk mill and granulating the powder in a fluidized bed by spraying on water as the granulating liquid.
f) Water-dispersible granules are also obtained by homogenizing and precomminuting
  25 parts by weight of a compound of the formula (I),
  5 parts by weight of the sodium salt of 2,2'-dinaphthylmethane-6,6'-disulfonate,
  2 parts by weight of the sodium salt of oleoylmethyltaurine,
  1 part by weight of polyvinyl alcohol,
  17 parts by weight of calcium carbonate and
  50 parts by weight of water
on a colloid mill, subsequently grinding the mixture on a bead mill and atomizing and drying the resulting suspension in a spray tower by means of a single substance nozzle.

C. BIOLOGICAL EXAMPLES

1. Herbicidal action, pre-emergence

Seeds or pieces or rhizome of mono- and dicotyledon weed plants were laid out in sandy loam soil in plastic pots and covered with soil. The compounds according to the invention, formulated in the form of wettable powders or emulsion concentrates, were then applied to the surface of the covering soil as an aqueous suspension or emulsion in various dosages, with an amount of water applied, when converted, of 600 to 800 l/ha.

After the treatment, the pots were placed in a greenhouse and kept under good growth conditions for the weeds. The plant damage or emergence damage was rated visually after emergence of the test plants after a test period of 3 to 4 weeks in comparison with untreated controls. As the test results show, the compounds according to the invention show a good herbicidal pre-emergence activity against a broad spectrum of gramineous weeds and broad-leafed weeds. For example, the compounds of Examples 8, 15, 22, 25, 30, 40, 44, 53, 55, 58, 59, 65, 72, 77, 87, 115 and 116 from Table 1 and the compounds of Examples 1, 7, 12, 16, 17, 20, 21, 22, 26, 28–30 and 32–35 from Table 2 have a very good herbicidal action against harmful plants such as Sinapis alba, Chrysanthemum segetum, Avena sativa, Stellaria media, Alopecurus myosuroides and Lolium multiflorum when applied pre-emergence in an amount of 0.3 kg and less of active substance per hectare.

2. Herbicidal action, post-emergence

Seeds or pieces of rhizome of mono- and dicotyledon weeds were laid out in sandy loam soil in plastic pots, covered with soil and grown in a greenhouse under good growth conditions. Three weeks after sowing, the test plants were treated in the three-leaf stage.

The compounds according to the invention, formulated as wettable powders or as emulsion concentrates, were sprayed onto the green parts of plants in various dosages with an amount of water applied of, when converted, 600 to 800 l/ha, and after the test plants had stood in a greenhouse for about 3 to 4 weeks under optimum growth conditions, the action of the preparations was rated visually in comparison with untreated controls. The compositions according to the invention also show a good herbicidal activity against a broad spectrum of economically important graminaceous weeds and broad-leafed weeds when applied post-emergence. For example, the compounds of Examples 8, 15, 22, 25, 30, 40, 44, 53, 55, 58, 59, 65, 72, 77, 87, 115 and 116 from Table 1 and the compounds of Examples 1, 7, 12, 16, 17, 20, 21, 22, 26, 28–30 and 32–35 have a very good herbicidal action against harmful plants such as Sinapis alba, Stellaria media, Alopecurus myosuroides and Lolium multiflorum, Chrysanthemum segetum and Avena sativa when applied postemergence in an amount of 0.3 kg or less of active substance per hectare.

3. Crop Plant Tolerability

In further tests in a greenhouse, seeds of a relatively large number of crop plants and weeds were laid out in sandy loam soil and covered with soil. Some of the pots were treated immediately as described under Section 1, and the others were placed in a greenhouse until the plants had developed two to three true leaves, and were then sprayed with the substances of the formula (I) according to the invention in various dosages as described under Section 2. Four to five weeks after the application and standing time in the greenhouse, it was found by means of visual rating that the compounds according to the invention left dicotyledon crops such as, for example, soya, cotton, rape, sugar beet and potatoes undamaged both pre- and post-emergence even at high dosages of active compound. Some substances furthermore even preserved graminaceous crops, such as, for example, barley, wheat, rye, sorghum/millet, maize or rice. The compounds of the formula (I) thus have a high selectivity when used for combating undesirable plant growth in agricultural crops.

What is claimed is:

1. A compound of the formula (II) or a salt thereof,

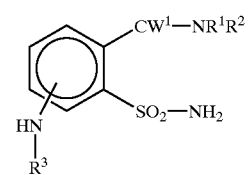

(II)

in which $W^1$ is an oxygen or sulfur atom, $R^1$ is H, $C_1$–$C_{24}$-alkyl, $C_2$–$C_{24}$-alkenyl, $C_2$–$C_{24}$-alkynyl, $C_1$–$C_{24}$-alkoxy, $C_2$–$C_{24}$-alkenyloxy $C_2$–$C_{24}$-alkynyloxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, O$R^6$, N$R^7R^8$, S$R^9$, SO—$R^{10}$ and SO$_2$—$R^{11}$, or unsubstituted or substituted phenyl, and has a total of up to 24 carbon atoms, $R^2$ is H, $C_1$–$C_{24}$-alkyl, $C_2$–$C_{24}$-alkenyl and $C_2$–$C_{24}$-alkynyl, where each of the three last-mentioned radicals is unsubstituted or substituted by one or more radicals from the group consisting of halogen, cyano, azido, CO—$R^{12}$, O$R^{13}$, N$R^{14}R^{15}$, S$R^{16}$, SO—$R^{17}$ and SO$_2$—$R^{18}$ and has a total of up to 24 carbon atoms, or the group $NR^1R^2$ is a saturated heterocyclic ring of three to eight ring atoms, which can have up to one further hetero atom in the ring from the group consisting of N, O and S and is unsubstituted or substituted by one or more radicals from the group consisting of $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, halogen, $NO_2$, $N_3$, CN and oxo, and has a total of up to 18 carbon atoms, $R^3$ is an acyl radical of the formula CO—$R^{19}$, CS—$R^{20}$, $SO_2$—$R^{21}$, SO—$R^{21}$ or C(=$NR^{21}$)—$R^{19}$, and has a total of up to 24 carbon atoms, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, $NR^{22}R^{23}$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or $COOCH_3$, $R^8$ is H, $C_1$–$C_5$-alkyl, $C_2$–$C_5$-alkenyl or $C_2$–$C_5$-alkynyl or the group $NR^7R^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals selected from the group consisting of halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkythio, $NO_2$, $N_3$, CN and oxo, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$, $R^{13}$ is a radical as defined for $R^6$, $R^{14}$ is a radical as defined for $R^7$, $R^{15}$ is a radical as defined for $R^8$, or the group $NR^{14}R^{15}$ is a group as defined for $NR^7R^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl) amino, N—$C_1$–$C_4$-alkoxy-N—$C_1$–$C_4$-alkylamino, where each of the thirteen last-mentioned radicals are unsubstituted or substituted by one or more radicals from the group consisting of halogen, cyano, azido, CO—$R^{24}$, $OR^{25}$, $NR^{26}R^{27}$, $SR^{28}$, $SOR^{29}$ and $SO_2R^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the six last-mentioned radicals are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the five last-mentioned radicals is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $N^{22}R^{23}$ is a heterocyclic ring as defined for $NR^7R^8$, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H or $C_1$–$C_3$-alkyl, or the group $NR^{26}R^{27}$ is a group as defined for $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, and $R^{30}$ is a radical as defined for $R^{29}$.

2. A compound of the formula (IV) or a salt thereof

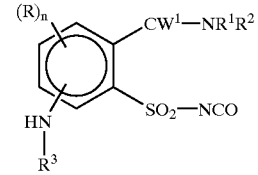

(IV)

in which $W^1$ is an oxygen or sulfur atom, n is 0, 1, 2 or 3,

R is halogen, alkyl or alkoxy, independently of other substituents R if n is greater than 1, $R^1$ is H, $C_1$–$C_{24}$-alkyl, $C_2$–$C_{24}$-alkenyl, $C_2$–$C_{24}$-alkynyl, $C_1$–$C_{24}$-alkoxy, $C_2$–$C_{24}$-alkenyloxy, $C_2$–$C_{24}$-alkynyloxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, $OR^6$, $NR^7R^8$, $SR^9$, SO—$R^{10}$ and $SO_2$—$R^{11}$, or unsubstituted or substituted phenyl, and has a total of up to 24 carbon atoms, $R_2$ is H, $C_1$–$C_{24}$-alkyl, $C_2$–$C_{24}$-alkenyl and $C_2$–$C_{24}$-alkynyl, where each of the three last-mentioned radicals is unsubstituted or substituted by one or more radicals from the group consisting of halogen, cyano, azido, CO—$R^{12}$, $OR^{13}$, $NR^{14}R^{15}$, $SR^{16}$, SO—$R^{17}$ and $SO_2$—$R^{18}$, and has a total of up to 24 carbon atoms, or the group $NR^1R^2$ is a saturated heterocyclic ring of three to eight ring atoms, which can have up to one further hetero-ring atom in the ring from the group consisting of N, O and S and is unsubstituted or substituted by one or more radicals from the group consisting of $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, halogen, $NO_2$, $N_3$, CN and oxo, and has a total of up to 18 carbon atoms, $R^3$ is an acyl radical of the formula CO—$R^{19}$, CS—$R^{20}$, $SO_2$—$R^{21}$, SO—$R^{21}$ or C(=$NR^{21}$)—$R^{19}$, and has a total of up to 24 carbon atoms, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, $NR^{22}R^{23}$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or $COOCH_3$, $R^8$ is H, $C_1$–$C_5$-alkyl, $C_2$–$C_5$-alkenyl or $C_2$–$C_5$-alkynyl or the group $NR^7R^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals selected from the group consisting of halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkythio, $NO_2$, $N_3$, CN and oxo, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$, $R^{13}$ is a radical as defined for $R^6$, $R^{14}$ is a radical as defined for $R^7$, $R^{15}$ is a radical as defined for $R^8$, or the group $NR^{14}R^{15}$ is a group as defined for $NR^7R^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl) amino, N—$C_1$–$C_4$-alkoxy-N—$C_1$–$C_4$-alkylamino, where each of the thirteen last-mentioned radicals are unsubstituted or substituted by one or more radicals from the group consisting of halogen, cyano, azido, CO—$R^{24}$, $OR^{25}$, $NR^{26}R^{27}$, $SR^{28}$, $SOR^{29}$ and $SO_2R^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the six last-mentioned radicals are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the five last-mentioned radicals is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $NR^{22}R^{23}$ is a heterocyclic ring as defined for $NR^7R^8$, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H or $C_1$–$C_3$-alkyl, or the group $R^{26}R^{27}$ is a group as defined for $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, and $R^{30}$ is a radical as defined for $R^{29}$.

3. A compound of the formula (VI) or a salt thereof (VI)

in which $W_1$ is an oxygen or sulfur atom, n is 0, 1, 2 or 3,

R is halogen, alkyl or alkoxy, independently of other substituents R if n is greater than 1, $R^1$ is H, $C_1$–$C_{24}$-alkyl, $C_2$–$C_{24}$-alkenyl, $C_2$–$C_{24}$-alkynyl, $C_1$–$C_{24}$-alkoxy, $C_2$–$C_{24}$-alkenyloxy, $C_2$–$C_{24}$-alkynyloxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, $OR^6$, $NR^7R^8$, $SR^9$, SO—$R^{10}$ and $SO^2$—$R^{11}$, or unsubstituted or substituted phenyl, and has a total of up to 24 carbon atoms, $R^2$ is H, $C_1$–$C_{24}$-alkyl, $C_2$–$C_{24}$-alkenyl and $C_2$–$C_{24}$-alkynyl, where each of the three last-mentioned radicals is unsubstituted or substituted by one or more radicals from the group consisting of halogen, cyano, azido, CO—$R^{12}$, $OR^{13}$, $NR^{14}R^{15}$, $SR^{16}$, SO—$R^{17}$ and $SO_2$—$R^{18}$, and has a total of up to 24 carbon atoms, or the group $NR^1R^2$ is a saturated heterocyclic ring of three to eight ring atoms, which can have up to one further hetero-ring atom in the ring from the group consisting of N, O and S and is unsubstituted or substituted by one or more radicals from the group consisting of $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, halogen, $NO_2$, $N_3$, CN and oxo, and has a total of up to 18 carbon atoms, $R^3$ is an acyl radical of the formula CO—$R^{19}$, CS—$R^{20}$, $SO_2$—$R^{21}$, SO—$R^{21}$ or C(=$NR^{21}$)—$R^{19}$, and has a total of up to 24 carbon atoms, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, $NR^{22}R^{23}$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or $COOCH_3$, $R^8$ is H, $C_1$–$C_5$-alkyl, $C_2$–$C_5$-alkenyl or $C_2$–$C_5$-alkynyl or the group $NR^7R^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals selected from the group consisting of halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkythio, $NO_2$, $N_3$, CN and oxo, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$, $R^{13}$ is a radical as defined for $R^6$, $R^{14}$ is a radical as defined for $R^7$, $R^{15}$ is a radical as defined for $R^8$, or the group $NR^{14}R^{15}$ is a group as defined for $NR^7R^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl) amino, N—$C_1$–$C_4$-alkoxy-N—$C_1$–$C_4$-alkylamino, where each of the thirteen last-mentioned radicals are unsubstituted or substituted by one or more radicals from the group consisting of halogen, cyano, azido, CO—$R^{24}$, $OR^{25}$, $NR^{26}R^{27}$, $SR^{28}$, $SOR^{29}$ and $SO_2R^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the six last-mentioned radicals are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the five last-mentioned radicals is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $N^{22}R^{23}$ is a heterocyclic ring as defined for $NR^7R^8$, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H or $C_1$–$C_3$-alkyl, or the group $NR^{26}R^{27}$ is a group as defined for $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, and $R^{30}$ is a radical as defined for $R^{29}$.

4. A compound of the formula (VIII) or a salt thereof

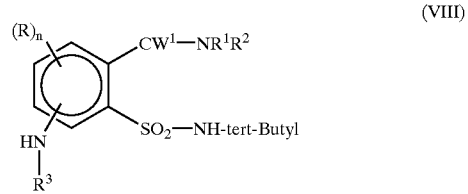

(VIII)

in which $W^1$ is an oxygen or sulfur atom, n is 0, 1, 2 or 3,

R is halogen, alkyl or alkoxy, independently of other substituents R if n is greater than 1, $R^1$ is H, $C_1$–$C_{24}$-alkyl, $C_2$–$C_{24}$-alkenyl, $C_2$–$C_{24}$-alkynyl, $C_1$–$C_{24}$-alkoxy, $C_2$–$C_{24}$-alkenyloxy, $C_2$–$C_{24}$-alkynyloxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, $OR^6$, $NR^7R^8$, $SR^9$, SO—$R^{10}$ and $SO_2$—$R^{11}$, or unsubstituted or substituted phenyl, and has a total of up to 24 carbon atoms, $R^2$ is H, $C_1$–$C_{24}$-alkyl, $C_2$–$C_{24}$-alkenyl and $C_2$–$C_{24}$-alkynyl, where each of the three last-mentioned radicals is unsubstituted or substituted by one or more radicals from the group consisting of halogen, cyano, azido, CO—$R^{12}$, OR$^{13}$, NR$^{14}$R$^{15}$, SR$^{16}$, SO—$R^{17}$ and SO$_2$—$R^{18}$, and has a total of up to 24 carbon atoms, or the group NR$^1$R$^2$ is a saturated heterocyclic ring of three to eight ring atoms, which can have up to one further hetero-ring atom in the ring from the group consisting of N, O and S and is unsubstituted or substituted by one or more radicals from the group consisting of $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, halogen, NO$_2$, N$_3$, CN and oxo, and has a total of up to 18 carbon atoms, $R^3$ is an acyl radical of the formula CO—$R^{19}$, CS—$R^{20}$, SO$_2$—$R^{21}$, SO—$R^{21}$ or C(=NR$^{21}$)—$R^{19}$, and has a total of up to 24 carbon atoms, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, NR$^{22}$R$^{23}$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—CH$_3$, CO—H or COOCH$_3$, $R^8$ is H, $C_1$–$C_5$-alkyl, $C_2$–$C_5$-alkenyl or $C_2$–$C_5$-alkynyl or the group NR$^7$R$^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals selected from the group consisting of halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkythio, NO$_2$, N$_3$, CN and oxo, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$, $R^{13}$ is a radical as defined for $R^6$, $R^{14}$ is a radical as defined for $R^7$, $R^{15}$ is a radical as defined for $R^8$, or the group NR$^{14}$R$^{15}$ is a group as defined for NR$^7$R$^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl) amino, N—$C_1$–$C_4$-alkoxy-N—$C_1$–$C_4$-alkylamino, where each of the thirteen last-mentioned radicals are unsubstituted or substituted by one or more radicals from the group consisting of halogen, cyano, azido, CO—$R^{24}$, OR$^{25}$, NR$^{26}$R$^{27}$, SR$^{28}$, SOR$^{29}$ and SO$_2$R$^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the six last-mentioned radicals are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the five last-mentioned radicals is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group NR$^{22}$R$^{23}$ is a heterocyclic ring as defined for NR$^7$R$^8$, $R^{25}$ is H, $C_1$–$C_3$-alkyl, $C_1$–$C_3$-alkoxy, NH$_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—CH$_3$ or CO—H, $R^{27}$ is H or $C_1$–$C_3$-alkyl, or the group NR$^{26}$R$^{27}$ is a group as defined for NR$^{22}$R$^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, and $R^{30}$ is a radical as defined for $R^{29}$.

5. A process for the preparation of a compound of the formula (I) or a salt thereof

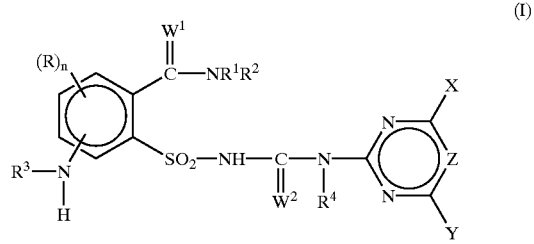

in which $W^1$ is an oxygen or sulfur atom, $W^2$ is an oxygen or sulfur atom, n is 0, 1, 2 or 3, R is halogen, alkyl or alkoxy, independently of other substituents R if n is greater than 1, $R^1$ is hydrogen, $C_1$–$C_{24}$-alkyl, $C_2$–$C_{24}$-alkenyl, $C_2$–$C_{24}$-alkynyl, $C_1$–$C_{24}$-alkoxy, $C_2$–$C_{24}$-alkenyloxy, $C_2$–$C_{24}$-alkynyloxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, $OR^6$, $NR^7R^8$, $SR^9$, SO—$R^{10}$ and $SO_2$—$R^{11}$, or unsubstituted or substituted phenyl, and has a total of up to 24 carbon atoms, $R^2$ is hydrogen, $C_1$–$C_{24}$-alkyl, $C_2$–$C_{24}$-alkenyl and $C_2$–$C_{24}$-alkynyl, where each of the three last-mentioned radicals is unsubstituted or substituted by one or more radicals from the group consisting of halogen, cyano, azido, CO—$R^{12}$, $OR^{13}$, $NR^{14}R^{15}$, $SR^{16}$, SO—$R^{17}$ and $SO_2$—$R^{18}$, and has a total of up to 24 carbon atoms or the group $NR^1R^2$ is a saturated heterocyclic ring of three to eight ring atoms, which can have up to one further hetero atoms in the ring from the group consisting of N, O and S and is unsubstituted or substituted by one or more radicals from the group consisting of $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, halogen, $NO_2$, $N_3$, CN and oxo, and has a total of up to 18 carbon atoms, $R^3$ is an acyl radical of the formula CO—$R^{19}$, CS—$R^{20}$, $SO_2$—$R^{21}$, SO—$R^{21}$ or C(=$NR^{21}$)—$R^{19}$, and has a total of up to 24 carbon atoms, $R^4$ is hydrogen, $C_1$–$C_{12}$-alkyl, $C_2$–$C_{12}$-alkenyl or $C_2$–$C_{12}$-alkynyl, X, Y independently of one another are halogen, $C_1$–$C_6$-alkyl, $C_1$–$C_6$-alkoxy, $C_1$–$C_6$-alkylthio, where each of the last three radicals mentioned is unsubstituted or substituted by one or more radicals from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, and Z is CH, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, $NR^{22}R^{23}$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or COO$CH_3$, $R^8$ is H, $C_1$–$C_5$-alkyl, $C_2$–$C_5$-alkenyl or $C_2$–$C_5$-alkynyl or the group $NR^7R^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals selected from the group consisting of halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkythio, $NO_2$, $N_3$, CN and oxo, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$ $R^{13}$ is a radical as defined for $R^6$ $R^{13}$ is a radical as defined for $R^7$, $R^{15}$ is a radical as defined for $R^8$, or the group $NR^{14}R^{15}$ is a group as defined for $NR^7R^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl)amino, N—$C_1$–$C_4$-alkoxy-N—$C_1$–$C_4$-alkylamino, where each of the 13 radicals mentioned last are unsubstituted or substituted by one or more radicals from the group consisting of halogen, cyano, azido, CO—$R^{24}$, $OR^{25}$, $NR^{26}R^{27}$, $SR^{28}$, $SOR^{29}$ and $SO_2R^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the radicals mentioned last are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the 5 radicals mentioned last is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $NR^{22}R^{23}$ is a heterocyclic ring as defined for $NR^7R^8$, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkynyl, or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H, $C_1$–$C_3$-alkyl, or the group $NR^{26}R^{27}$ is a group as defined for $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, $R^{30}$ is a radical as defined for $R^{29}$, which comprises:

a) reacting a compound of the formula (III)

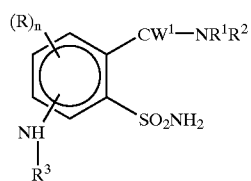

(II)

with a heterocyclic carbamate of the formula (III),

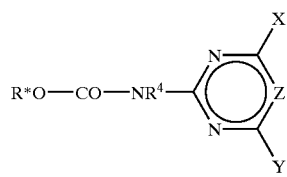

(III)

in which R* is unsubstituted or substituted phenyl or $C_1$–$C_4$-alkyl, or b) reacting a sulfonyl isocyanate of the formula (IV)

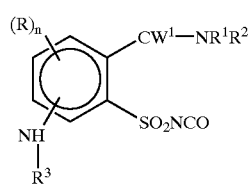

(IV)

with a heterocyclic amine of the formula (V)

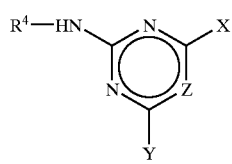

(V)

or c) reacting a sulfonyl chloride of the formula (VI)

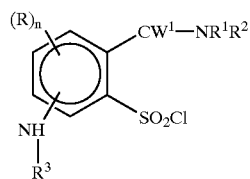

(VI)

with a heterocyclic amine of the above formula (V) in the presence of a cyanate, or d) reacting a sulfonamide of the above formula (II) with a (thio)isocyanate of the formula (VII)

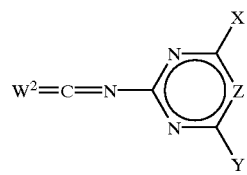

(VII)

in the presence of a suitable base, such as, for example, such as potassium carbonate or triethylamine, in which, in the above formulae (II) to (VII), the radicals R, $R^1$, $R^2$, $R^3$, $R^4$, $W^1$, $W^2$, X, Y, and Z and the index n are as defined in formula (I), and where compounds of the formula (I) in which $W^2$ is an oxygen atom are first obtained in variants a)–c).

6. A compound of the formula

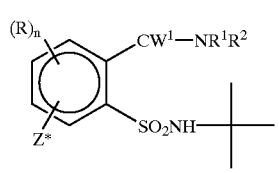

(VIII)

in which, $Z^*$ is $NHR^3$, $NH_2$ or $NO_2$;

$W^1$ is an oxygen or a sulfur atom;

n is 0, 1, 2 or 3;

R is halogen, alkyl or alkoxy, independently of other substituents R if n is greater than 1, $R^1$ is hydrogen, $C_1$–$C_{24}$-alkyl, $C_2$–$C_{24}$-alkenyl, $C_2$–$C_{24}$-alkynyl, $C_1$–$C_{24}$-alkoxy, $C_2$–$C_{24}$-alkenyloxy, $C_2$–$C_{24}$-alkynyloxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, $OR^6$, $NR^7R^8$, $SR^9$, SO—$R^{10}$ and $SO_2$—$R^{11}$, or unsubstituted or substituted phenyl, and has a total of up to 24 carbon atoms, $R^2$ is hydrogen, $C_1$–$C_{24}$-alkyl, $C_2$–$C_{24}$-alkenyl and $C_2$–$C_{24}$-alkynyl, where each of the three last-mentioned radicals is unsubstituted or substituted by one or more radicals from the group consisting of halogen, cyano, azido, CO—$R^{12}$, $OR^{13}$, $NR^{14}R^{15}$, $SR^{16}$, SO—$R^{17}$ and $SO_2$—$R^{18}$, and has a total of up to 24 carbon atoms or the group $NR^1R^2$ is a saturated heterocyclic ring of three to eight ring atoms, which can have up to one further hetero atoms in the ring from the group consisting of N, O and S and is unsubstituted or substituted by one or more radicals from the group consisting of $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, halogen, $NO_2$, $N_3$, CN and oxo, and has a total of up to 18 carbon atoms, $R^3$ is an acyl radical of the formula CO—$R^{19}$, CS—$R^{20}$, $SO_2$—$R^{21}$, SO—$R^{21}$ or C(=$NR^{21}$)—$R^{19}$, and has a total of up to 24 carbon atoms, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, $NR^{22}R^{23}$ or OH, $R^6$ is H, $C_1$–$C_5$-alkyl, $C_1$–C 5-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or $COOCH_3$, $R^8$ is H, $C_1$–$C_5$-alkyl, $C_2$–$C_5$-alkenyl or $C_2$–$C_5$-alkynyl, or the group $NR^7R^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals selected from the group consisting of halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkythio, $NO_2$, $N_3$, CN and oxo, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$, $R^{13}$ is a radical as defined for $R^6$, $R^{14}$ is a radical as defined for $R^7$, $R^{15}$ is a radical as defined for $R^8$, or the group $NR^{14}R^{15}$ is a group as defined for $NR^7R^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl) amino, N—$C_1$–$C_4$-alkoxy-N—$C_1$–$C_4$-alkylamino, where each of the 13 radicals mentioned last are unsubstituted or substituted by one or more radicals from the group consisting of halogen, cyano, azido, CO—$R^{24}$, OR$^{25}$, $NR^{26}R^{27}$, SR$^{28}$, SOR$^{29}$ and $SO_2R^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxym, or $C_2$–$C_5$-alkynoxy, where each of the radicals mentioned last are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the 5 radicals mentioned last is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $NR^{22}R^{23}$ is a heterocyclic ring as defined for $NR^7R^8$, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H, $C_1$–$C_3$-alkyl, or the group $NR^{26}R^{27}$ is a group as defined for $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, $R^{30}$ is a radical as defined for $R^{29}$.

7. A compound of the following formula or a salt thereof,

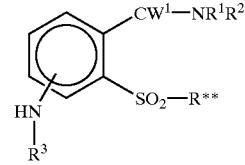

in which $W^1$ is an oxygen or sulfur atom $R^1$ is hydrogen, $C_1$–$C_{24}$-alkyl, $C_2$–$C_{24}$-alkenyl, $C_2$–$C_{24}$-alkynyl, $C_1$–$C_{24}$-alkoxy, $C_2$–$C_{24}$-alkenyloxy, $C_2$–$C_{24}$-alkynyloxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, OR$^6$, $NR^7R^8$, SR$^9$, SO—$R^{10}$ and $SO_2$—$R^{11}$, or unsubstituted or substituted phenyl, and has a total of up to 24 carbon atoms, $R^2$ is hydrogen, $C_1$–$C_{24}$-alkyl, $C_2$–$C_{24}$-alkenyl and $C_2$–$C_{24}$-alkynyl, where each of the three last-mentioned radicals is unsubstituted or substituted by one or more radicals from the group consisting of halogen, cyano, azido, CO—$R^{12}$, OR$^{13}$, $NR^{14}R^{15}$, SR$^{16}$, SO—$R^{17}$ and $SO_2$—$R^{18}$, and has a total of up to 24 carbon atoms, or the group $NR^1R^2$ is a saturated heterocyclic ring of three to eight ring atoms, which can have up to one further hetero atoms in the ring from the group consisting of N, O and S and is unsubstituted or substituted by one or more radicals from the group consisting of $C_1$–$C_6$-alkyl, $C_1$–$C_4$-haloalkyl, $C_1$–$C_4$-alkoxy, $C_1$–$C_4$-haloalkoxy, $C_1$–$C_4$-alkylthio, halogen, $NO_2$, $N_3$, CN and oxo, and has a total of up to 18 carbon atoms, $R^3$ is an acyl radical of the formula CO—$R^{19}$, CS—$R^{20}$, $SO_2$—$R^{21}$, SO—$R^{21}$ or C(=NR$^{21}$)—$R^{19}$, and has a total of up to 24 carbon atoms, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, $NR^{22}R^3$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or COOCH$_3$, $R^8$ is H, $C_1$–$C_5$-alkyl, $C_2$–$C_5$-alkenyl or $C_2$–$C_5$-alkynyl or the group $NR^7R^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals selected from the group consisting of halogen, $C_1$–$C_6$-alkyl, $C_1$–$C_4$-haloalkyl, $C_1$–$C_4$-alkoxy, $C_1$–$C_4$-haloalkoxy, $C_1$–$C_4$-alkythio, $NO_2$, $N_3$, CN and oxo, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl, $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$, $R^{13}$ is a radical as defined for $R^6$, $R^{14}$ is a radical as defined for $R^7$, $R^{15}$ is a radical as defined for $R^8$, or the group $NR^{14}R^{15}$ is a group as defined for $NR^7R^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$-$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl)amino, N—$C_1$–$C_4$-alkoxy-N—$C_1$–$C_4$-alkylamino, where each of the 13 radicals mentioned last are unsubstituted or substituted by one or more radicals from the group consisting of halogen, cyano, azido, CO—$R^{24}$, OR$^{25}$, NR$^{26}$R$^{27}$, SR$^{28}$, SOR$^{29}$ and SO$_2$R$^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the radicals mentioned last are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$-$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the 5 radicals mentioned last is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $NR^{22}R^{23}$ is a heterocyclic ring as defined for $NR^7R^8$, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H, $C_1$–$C_3$-alkyl, or the group $NR^{26}R^{27}$ is a group as defined for $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, $R^{30}$ is a radical as defined for $R^{29}$, and R** is $NH_2$, NCO, Cl or NH-tert-butyl.

8. A compound as claimed in claim 7, wherein $R^1$ is methyl and $R^2$ is methyl.

9. A compound as claimed in claim 8, wherein $R^3$ is formyl.

10. A compound as claimed in claim 8, wherein $R^3$ is acetyl.

11. A compound as claimed in claim 8, wherein $R^3$ is ethylcarbonyl.

12. A compound as claimed in claim 8, wherein $R^3$ is isopropylcarbonyl.

13. A compound as claimed in claim 8, wherein $R^3$ is triflouromethylcarbonyl.

14. A compound as claimed in claim 8, wherein $R^3$ is methoxycarbonyl.

15. A compound as claimed in claim 8, wherein $R^3$ is ethoxycarbonyl.

16. A sodium salt of the compound as claimed in claim 9.

17. A sodium salt of the compound as claimed in claim 10.

18. A sodium salt of the compound as claimed in claim 11.

19. A sodium salt of the compound as claimed in claim 12.

20. A sodium salt of the compound as claimed in claim 13.

21. A sodium salt of the compound as claimed in claim 14.

22. A sodium salt of the compound as claimed in claim 15.

23. The compound as claimed in claim 7 or a salt thereof, in which $R^1$ is H, $C_1$–$C_{12}$-alkyl, $C_2$–$C_{12}$-alkenyl, $C_2$–$C_{12}$-alkynyl, $C_1$–$C_{12}$-alkoxy, $C_2$–$C_{12}$-alkenoxy, $C_2$–$C_{12}$-alkynoxy, $C_3$–$C_8$-cycloalkyl or $C_5$–$C_8$-cycloalkenyl, where each of the eight last-mentioned radicals is unsubstituted or substituted by one or more radicals from the group consisting of halogen, cyano, azido, CO—$R^5$, OR$^6$, NR$^7$R$^8$, SR$^9$, SO—R$^{10}$ and SO$_2$—R$^{11}$, or unsubstituted or substituted phenyl, $R_2$ is H, $C_1$–$C_{12}$-alkyl, $C_2$–$C_{12}$-alkenyl or $C_2$–$C_{12}$-alkynyl, where each of the three last-mentioned radicals is unsubstituted or substituted by one or more radicals from the group consisting of halogen, cyano, azido, COR$^{12}$, OR$^{13}$, NR$^{14}$R$^{15}$, SR$^{16}$, SO—R$^{17}$ and SO$_2$—R$^{18}$, or the group $NR^1R^2$ is a saturated heterocyclic ring of four to eight ring atoms, which optionally has up to one further hetero atom in the ring from the group consisting of N, O and S and is unsubstituted or substituted by one or more radicals from the group consisting of halogen, $C_1$–$C_6$-alkyl, $NO_2$, $N_3$ and CN, $R^3$ is CO—$R^{19}$, CS—$R^{20}$, $SO_2$—$R^{21}$, SO—$R^{21}$ or C(=NR$^{21}$)—R$^{19}$, $R^5$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy, $C_2$–$C_5$-alkynoxy, NR$^{22}$R$^{23}$ or OH, $R^6$ is H, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^7$ is H, $C_1$–$C_5$-alkyl, $C_2$–$C_5$-alkenyl, $C_2$–$C_5$-alkynyl, $C_1$–$C_5$-alkoxy, CO—$CH_3$, CO—H or COOCH$_3$, $R^8$ is H, $C_1$–$C_5$-alkyl, $C_2$–$C_5$-alkenyl or $C_2$–$C_5$-alkynyl or the group $NR^7R^8$ is a heterocyclic ring selected from the group consisting of the heteroaromatic or non-heteroaromatic rings pyridyl, pyrimidinyl, pyridazinyl, pyrazinyl, thiazolyl, oxazolyl, pyrrolyl, pyrazolyl, imidazolyl, pyrrolidyl, piperidyl, piperazinyl and morpholinyl, where each of the heterocyclic rings is unsubstituted or substituted by one or more radicals from the group consisting of halogen, $C_1$–$C_6$-alkyl, $NO_2$, $N_3$ and CN, $R^9$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{10}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{11}$ is $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $C_1$–$C_5$-alkoxyalkyl, $C_3$–$C_8$-cycloalkyl or $C_5$–$C_8$-cycloalkenyl, $R^{12}$ is a radical as defined for $R^5$, $R^{13}$ is a radical as defined for $R^6$, $R^{14}$ is a radical as defined for $R^7$, $R^{15}$ is a radical as defined for $R^8$, or the group $NR^{14}R^{15}$ is a group as defined for $NR^7R^8$, $R^{16}$ is a radical as defined for $R^9$, $R^{17}$ is a radical as defined for $R^{10}$, $R^{18}$ is a radical as defined for $R^{11}$, $R^{19}$ is H, $C_1$–$C_{12}$-alkyl, $C_2$–$C_{12}$-alkenyl, $C_2$–$C_{12}$-alkynyl, $C_1$–$C_{12}$-alkoxy, $C_1$–$C_{12}$-alkylthio, $C_2$–$C_{12}$-alkenoxy, $C_2$–$C_{12}$-alkynoxy, $C_3$–$C_8$-cycloalkyl, $C_5$–$C_8$-cycloalkenyl, $C_1$–$C_{12}$-alkylamino, di($C_1$–$C_6$-alkyl)amino, N—$C_1$–$C_4$-alkoxy-N—$C_1$–$C_4$-alkylamino, where each of the thirteen radicals last-mentioned are unsubstituted or substituted by one or more radicals from the group consisting of halogen, cyano, azido, CO—$R^{24}$, $OR^{25}$, $NR^{26}R^{27}$, $SR^{28}$, $SOR^{29}$ and $SO_2R^{30}$, or an unsubstituted or substituted phenyl, phenoxy or phenylamino radical, $R^{20}$ is a radical as defined for $R^{19}$, $R^{21}$ is a radical as defined for $R^{11}$, $R^{22}$ is H, $C_1$–$C_5$-alkyl, $C_2$–$C_5$-alkenyl, $C_2$–$C_5$-alkynyl, $C_1$–$C_5$-alkoxy, $C_2$–$C_5$-alkenoxy or $C_2$–$C_5$-alkynoxy, where each of the six last-mentioned radicals are unsubstituted or substituted by one or more radicals from the group consisting of halogen, cyano, azido, amino, mono- and disubstituted amino, $C_1$–$C_3$-alkyl, $C_1$–$C_3$-alkoxy, $C_1$–$C_3$-alkylsulfonyl, $C_1$–$C_3$-alkylsulfinyl and $C_1$–$C_3$-alkylthio, $R^{23}$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, where each of the five radicals last-mentioned is unsubstituted or substituted by one or more radicals from the group consisting of halogen, cyano, azido, amino, mono- and disubstituted amino, $C_1$–$C_3$-alkoxy, $C_1$–$C_3$-alkylthio, $C_1$–$C_3$-alkylsulfonyl and $C_1$–$C_3$-alkylsulfinyl, or the group $NR^{22}R^{23}$ is a heterocyclic ring as defined for $NR^7R^8$, $R^{24}$ is H, $C_1$–$C_3$-alkyl, $C_1$–$C_3$-alkoxy, $NH_2$ or mono- or disubstituted amino, $R^{25}$ is H, $C_1$–$C_5$-alkyl, $C_2$–$C_5$-alkenyl, $C_2$–$C_5$-alkynyl, $C_1$–$C_5$-haloalkyl, $C_2$–$C_5$-haloalkenyl or $C_2$–$C_5$-haloalkynyl, $R^{26}$ is H, $C_1$–$C_3$-alkyl, $C_1$–$C_3$-alkoxy, CO—$CH_3$ or CO—H, $R^{27}$ is H or $C_1$–$C_3$-alkyl, or the group $NR^{26}R^{27}$ is a group as defined for $NR^{22}R^{23}$, $R^{28}$ is H, $C_1$–$C_3$-alkyl, $C_1$–$C_3$-haloalkyl, $C_2$–$C_5$-alkenyl, $C_2$–$C_5$-haloalkenyl, $C_2$–$C_5$-alkynyl or $C_2$–$C_5$-haloalkynyl, $R^{29}$ is $C_1$–$C_5$-alkyl, $C_1$–$C_5$-haloalkyl, $C_2$–$C_5$-alkenyl, $C_2$–$C_5$-haloalkyl, $C_2$–$C_5$-alkynyl or $C_2$–$C_5$-haloalkynyl, $R^{30}$ is as defined for $R^{29}$, and wherein the term unsubstituted or substituted phenyl is phenyl which is unsubstituted or substituted by one or more radicals selected from the group consisting of halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, hydroxy, amino, ($C_1$–$C_4$-alkoxy)-carbonyl, ($C_1$–$C_4$-alkyl)-carbonyl, formyl, carbamoyl, mono- and di-($C_1$–$C_4$-alkyl)-aminocarbonyl, mono-and di-($C_1$–$C_4$-alkyl)-amino, ($C_1$–$C_4$-alkyl)-carbonylamino, formylamino, $C_1$–$C_4$-alkylsulfinyl, $C_1$–$C_4$-haloalkylsulfinyl, $C_1$–$C_4$-alkylsulfonyl, $C_1$–$C_4$-haloalkylsulfonyl, $NO_2$, $N_3$ and CN.

24. A compound or a salt thereof as claimed in claim 7, in which the group $NHR^3$ on the phenyl ring is in the meta-position relative to the $SO_2$ group and in the para-position relative to the group $CW^1$—$NR^1R^2$, and in which $W^1$ is an oxygen atom, $R^1$ is H, $C_1$–$C_2$-alkyl, $C_1$–$C_2$-alkoxy or phenyl which is unsubstituted or substituted by one or more radicals from the group consisting of halogen, $C_1$–$C_2$-alkyl, $C_1$–$C_2$-alkoxy, $C_1$–$C_2$-haloalkyl and $C_1$–$C_2$-haloalkoxy, $R^2$ is H, $C_1$–$C_2$-alkyl or $C_1$–$C_2$-alkoxy, or the group $NR^1R^2$ is a saturated heterocyclic ring of five or six ring atoms, which can contain up to one further hetero atom in the ring from the group consisting of N, O and S and is unsubstituted or substituted by one or more $C_1$–$C_2$-alkyl radicals, $R^3$ is CO—$R^{19}$, CS—$R^{20}$ or $SO_2$—$R^{21}$, $R^{19}$ is H, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_2$–$C_4$-alkenoxy, $C_2$–$C_4$-alkynoxy, $C_3$–$C_6$-cycloalkyl, $C_1$–$C_4$-alkylamino, di($C_1$–$C_4$-alkyl)amino, N—$C_1$–$C_2$-alkoxy-N—$C_1$–$C_2$-alkylamino, where each of the ten radicals last-mentioned is unsubstituted or substituted by one or more radicals from the group consisting of halogen and $C_1$–$C_4$-alkoxy, or a phenyl or phenyloxy radical, which is unsubstituted or substituted by radicals from the group consisting of halogen, $C_1$–$C_2$-alkyl, $C_1$–$C_2$-alkoxy, $C_1$–$C_2$-haloalkyl and $C_1$–$C_2$-haloalkoxy, $R^{20}$ is a radical as defined for $R^{19}$, and $R^{21}$ is $C_1$–$C_3$-alkyl, $C_1$–$C_3$-haloalkyl or $C_1$–$C_3$-alkoxy-$C_1$–$C_2$-alkyl.

25. The compound according to claim 23, wherein R** is $NH_2$.

26. The compound according to claim 24, wherein R** is $NH_2$.

27. The compound according to claim 23, wherein R** is NCO or Cl.

28. The compound according to claim 24, wherein R** is NCO or Cl.

29. The compound according to claim 23, wherein R** is NH-t-butyl.

30. The compound according to claim 24, wherein R** is NH-t-butyl.

* * * * *